United States Patent [19]

Coucouvanis et al.

[11] Patent Number: 6,111,123
[45] Date of Patent: Aug. 29, 2000

[54] SALICYLALDIMINE-CROWN ETHER DITOPIC RECEPTOR MOLECULES

[75] Inventors: Dimitri Coucouvanis; Dell Rosa, both of Ann Arbor, Mich.

[73] Assignee: The Regents of the University of Michigan, Ann Arbor, Mich.

[21] Appl. No.: 09/062,956

[22] Filed: Apr. 20, 1998

[51] Int. Cl.$^7$ .............................. C07F 13/00; C07F 15/00; A61K 9/127
[52] U.S. Cl. .............................................. 556/45; 424/450
[58] Field of Search .............................. 556/45, 113, 150; 424/450

[56] References Cited

PUBLICATIONS

Hackh's Chemical Dictionary, Fourth Edition, McGraw–Hill Book Co., New York, 1969.
Fyles and Zeng, "Molecular Recognition–Controlled Membrane Disruption by a Bis (Crown Ether) Bola–Amphiphile," *Chem. Commun.* 2295–2296 [1996].
Papahadjopoulos and Gabizon, *Liposomes as Tools in Basic Research and Industry*, J.A. Phillippot Ed., [1995].
Behr and Lehn, "Transport of Amino Acids through Organic Liquid Membranes," *J. Am. Chem. Soc.* 95:6108–6110 [1973].
Newcomb et al., "Enantiomer Differentiation in Transport through Bulk Liquid Membranes," *J. Am. Chem. Soc.* 101:7367–7369 [1974].
Rebek et al., "Convergent Functional Groups. 4. Recognition and Transport of Amino Acids across a Liquid Membrane," *J. Am. Chem. Soc.* 109:2432–2434 [1987].
Reetz et al., "Highly Effecient Transport of Amino Acids through Liquid Membranes via Three–Component Supramolecules,"*J. Am. Chem. Soc.* 116:11588–11589 [1994].

Paugam et al., Facilitated Catecholamine Transport through Bulk and Polymer–Supported Liquid Membranes, *J. Am. Chem. Soc.* 118:9820–9825 [1996].
Rudkevich et al., "Bifunctional Recognition: Simultaneous Transport of Cations and Anions through a Supported Liquid Membrane," *J. Am. Chem. Soc.* 117:6124–6125 [1995].
Schmidtchen, "Tetazac: A Novel Artificial Receptor for Binding ω–Amino Carboxylates," *J. Org. Chem.* 51:5161 [1986].
Gok et al., "The Interaction of Cu(II) and Ni(II) with Oxygen–Nitrogen Mixed donor Macrocycles Containing Grown Ether Moities," *Synth. React. Inorg. Met–Org. Chem.* 27:331–345 [1997].
Karabocek et al., "Mono– and Dinuclear Copper(II) Complexes of a Schiff Base Ligand, 4', 5'–Bis(Salicylideneimino)Benzo–15–Crown–5," *Polyhedron* 16:1771–1774 [1997].
Gul et al., "Synthesis of 4', 5'–Bis(Salicylideneimino)Benzo(15–Crown–15) and Its Complexes with Uranyl(VI), Copper(II), Nickel (II) and Cobalt (II)," *Synth. React. Inorg. Met–Org. Chem.* 16:871–884 [1986].
Van Staveren, et. al., "Cocomplexationof Neutral Guests and Electrophilic Metal Cation in Synthetic Macrocyclic Hosts," *J. Am. Chem. Soc.* 110:4994–5008 [1988].

(List continued on next page.)

*Primary Examiner*—Porfirio Nazario-Gonzalez
*Attorney, Agent, or Firm*—Medlen & Carroll, LLP

[57] ABSTRACT

The present invention relates generally to carriers for transport of amino acid, amino acid derivatives and other biologically important molecules such as catecholamines and neurotransmitters. In particular, the present invention relates to ditopic receptor molecules that contain salicylaldimine and crown-ether subunits, and complexed to metal ions. The compounds of the present invention were shown to have efficient transport properties for zwitterions.

22 Claims, 6 Drawing Sheets

OTHER PUBLICATIONS

Sessler et al., "Synthesis, Characterization, and $^{23}$Na NMR Studies of a Novel Dysprosium(III) Crown Ether Texaphyrin," *New J. Chem.* 16:541–544 [1992].

Sielcken et al.,"Crown–Ether Substituted Phthalocyanines. COntrol Supramolecular Organization by Monovalent and Divalent Metal Salts," *Recl. Trav. Chim. Pays–Bas,* 109:425–428 [1990].

Gasyna et al., "Optical Absorption and Magnetic Circular Dichroism Studies of Hydrogen, Monomeric and Dimeric Phthalocyamines," *J. Chem. Soc. Dalton Trans.* 2397–2405 [1989].

Sielcken et al., "Synthesis and aggregation Behavior of Hosts Containing Phthalocyanine and Crown Ether Subunits," *J. Am. Chem. Soc.* 109:4261–4265 [1987].

Kobayashi and Lever, "Cation– or Solvent–Indued Supermolecular Phthalocyanine Formulation: Crown Ether Substituted Phthalocynines," *J. Am. Chem. Soc.* 109:7433–7441 [1987].

Kobayashi and Nishiyama, "A Copper Phthalalocyanine with Four Crown Ether Voids," *J. Chem. Soc. Chem. Commun.* 1462–1465 [1986].

Lehn, "Cryptates: Inclusion Complexes of MAcropolycyclic Receptor Molecules," *Pure and Appl. Chem.* 50:871–892 [1978].

Can and Bekåroğlu, "Synthesis and Characteriazation of a Crown–e/Ether Substituted Salicylaldmine Schiff–Base Ligand and Its Complexes with Cobalt(II), Nickel(II), and URany(II)," *J. Chem. Soc. Dalton Trans.* 2831–2835 [1988]).

Bitter et al., Synthethis of Ion Selective Crown Ethers and Their Effect on the Permeability of Some Liposomes, *Bio–Organic Heterocycles Synthetic, Physical Organic and Pharmacological Aspects,* Plas et al., ed., pp. 397–400 [1984].

Kobuke and Yamamoto, "Cation Transport by Modified DiBenzo–18–Crown–6 through Lecithin Liposomal Membrane," *Bioor. Chem.* 18:283–290 [1990].

Hamilton and Kaler, "Facilitated Ion Transport Through Thin Bilayers," *J. Membr. Sci.* 54:259–269 [1990].

Darwish and Uchegbu, The Evaluation of Crown Ether Based Niosomes as Cation Containing And Cation Sensitive Drug Delivery Systems, *Int. J. Pharm.* 159:207–213 [1997].

Grandjean, "Pr$^{3+}$ Transport Across Phosphatidylcholine Vesicles Mediated by Open Crown Syntheitc Ionophores," *Chem. Phys. Lipids* 41:309–314 [1986.

Muñoz et al., "Ultrathin Monolayer Lipid Membranes From a Family of Crown Ether–Based Bola–Amphiphiles," *J. Am. Chem. Soc.* 115:1705–1711 [1993].

Muñoz et al., "Lariat Ether Bola–Amphiphiles: Formation of Crown Ether Based Bola–Amphisomes," *J. Chem. Soc. Chem. Commun.* 520–522 [1992.

Paugam et al., "Facilitated Catecholamine Transport Bulk and Polymer–Supported Liquid Membranes," *J. Am. Chem. Soc.* 118:9820–9825.

Bailey, J.L., "Determination of Nitrogen," *Techniques in Protein Chemistry* 2nd Ed.

Maurya and Maurya, "Coordination Chemistry of Schiff Base Complexes of Uranium," *Rev. in Inorg. Chem.* 15:59–60 (1995).

Raymo and Stoddart, "Second–Sphere Coordination," *Chem. Ber.* 129:981–990 (1996).

Stack et al., "Structural and Spectroscopic Characterization of Chiral Ferric Tris– Catecholamides: Unraveling the Design of Enterobactin," *J. Am. Chem. Soc.* 114:1512–1514 (1992).

Voyer and Guerin, "Chiral Recognition Ability of Peptide–based Molecular Receptors," *Chem. Commun.* 2329–2330 (1997).

Scheerder et al., "Synthetic Receptors for Anion Complexation," *Recl. Trav. Chim. Pays–Bas* 115:307–320 (1996).

Larrow and Jacobsen, "A practical method for the large–scale preparation of [N, N'–Bis(3,5–di–tert–butylsalicylidene)–1,2cyclohexanediaminato(2)]manganese(II) Chloride, a highly effective enantioselective epoxidation catalyst," *J. Org. Chem.* 59:1939–1942 (1994).

Van Veggel et al., "Metallomacrocycles: Supermolecular chemistry with hard and soft metal cations in action," *Chemical Reviews* 94:279–299.

Beer, "Redox responsive macrocyclic receptor molecules containing transition metal redox centres," *Chem. Soc. Rev.* 18:409–450 (1989).

Christensen et al, "The synthesis and ion binding of synthetic multidentate macrocyclic compounds," *Chemical Reviews,* 74:351–384 (1973).

Ciringh et al., "Multinuclear Paramagnetic NMR Spectra and Solid State X–ray Crystallographic Characterization of Manganese (III) Schiff–Base Complexes," *Inorg. Chem.* 36:4968–4982 (1997).

SALICYLALDIMINE-CROWN ETHER DITOPIC RECEPTOR MOLECULES

This invention was made with government support under CHE9307382 awarded by the National Science Foundation. The government rights in the invention.

FIELD OF THE INVENTION

The present invention relates to the development of carriers that are capable of interacting at more than one site and are effective in transporting zwitterions and other biologically important molecules. In particular, the present invention relates to ditopic receptor molecules that contain salicylaldimine and crown ether subunits, and complexed to metal ions.

BACKGROUND OF THE INVENTION

Drug delivery using liposomes relies on cell uptake of the liposome by fusion or phagocytosis. Unfortunately, stabilized liposomes capable of specific cell targeting in vivo are resistant to these uptake mechanisms. A solution to this impasse is to couple molecular recognition of the target to the release of liposome contents. (Fyles and Zeng, *Chem. Commun.* 2295–2296 [1996]). The introduction of carriers capable of molecular recognition into liposomes that contain a drug of interest in the inner compartment of the liposomes introduces the potential of controlled release of the drug over a period of time. This approach to drug release has been used with other carriers in cancer chemotherapy. (See, Papahadjopoulos and Gabizon, *Liposomes as Tools in Basic Research and Industry*, J. A. Phillippot Ed., 1995).

The development of carriers that can recognize and transport common aminoacids as well as specific physiologically important molecules, such as the catecholamines and neurotransmitters, is in its infancy. Pioneering studies by Lehn and Cram have examined the transport of ammonium salts of aminoacids under acidic conditions across organic solvent membranes. (Behr and Lehn, *J. Am. Chem. Soc.* 95:6108 [1973]; Newcomb et al., *J. Am. Chem. Soc.* 101:7367 [1979]). The transport of hydrophobic aminoacids from aqueous solution at the isoelectric point across a $CHCl_3$ solution that contained a Kemp's triacidacridine 2:1 condensate has been reported. (Rebek et al., *J. Am. Chem. Soc.* 109:2432 [1987]. The transport of phenylalanine in a neutral pH transport system, through chloroform membranes by cooperative ditopic interactions between the aminoacid, arylboronic acids and crown ethers has also been reported. (Reetz et al., *J. Am. Chem. Soc.* 116:11588–11589 [1994]). A similar system but with the boronic acids covalently attached to crown ethers was found effective in ditopic facilitated transport of catecholamines across bulk and polymer supported membranes. (Paugam et al., *J. Am. Chem. Soc.* 118:9820–9825 [1996]). A neutral bifunctional receptor that contains calix[4]phosphate and an appended uranyl salphen unit was found effective in the simultaneous transport of anions and cations (Rudkevich et al., *J. Am. Chem. Soc.* 116:6124–6125 [1995]. A ditopic receptor, that consists of a macrotricyclic quaternary ammonium unit bridged via a xylyl bridge to an aza crown ether, has been reported to interact with co-aminocarboxylates. (Schmidtchen, *J. Org. Chem.* 51:5161 [1986]). However, none of these are effective in transporting zwitterions at any significant rate.

Complexes of crown-ether functionalized planar multidentate complexes have been reported, which include derivatives of salicylideneimines, porphyrins and phthalocyanines. See e.g., Gok et al., *Synth. React. Inorg. Met-Org. Chem.* 27:331–345 [1997]; Karabocek et al., *Polyhedron* 16:1771–1774 [1997]; Gul et al., *Synth. React. Inorg. Met-Org Chem.* 16:871–884 [1986]; Van Staveren, et. al., *J. Am. Chem. Soc.* 110:4994 [1988]; Sessler et al., *New J. Chem.* 16:541–544 [1992]; Sielcken et al., *Recl. Trav. Chim. Pays-Bas,* 109:425 [1990]; Gasyna et al., *J. Chem. Soc. Dalton Trans.* 2397 [1989]; Sielcken et al., *J. Am. Chem. Soc.* 109:4261 [1987]; Kobayashi and Lever, *J. Am. Chem. Soc.* 109:7433[1987]; Kobayashi and Nishiyama, *J. Chem. Soc. Chem. Commun.* 1462 [1986]; Lehn, *Pure and Appl. Chem.* 50:871–892 [1978]; Can and Bekåroǧlu, *J. Chem. Soc. Dalton Trans.* 2831–2835 [1988]). Furthermore, a number of carriers have been reported that contain crown ethers and transport cations, particularly alkali metal ions, across artificial membranes. (See e.g., Bitter et al., *Bio-Organic Heterocycles Synthetic, Physical Organic and Pharmacological Aspects*, Plas et al., ed., pp.397–400 [1984]; Kobuke and Yamamoto, *Bioorg. Chem.* 18:283–290 [1990]; Hamilton and Kaler, *J. Membr. Sci.* 54:259–269 [1990]; Darwish and Uchegbu, *Int. J. Pharm.* 159:207–213 [1997]; Grandjean *Chem. Phys. Lipids* 41:309–314 [1986]). However, none of these carriers are capable of interacting at more than one site, and none of them are effective in transporting zwitterions at any significant rate.

Crown ether-based bola-amphiphiles have also been reported. (See e.g., Muñoz et al., *J. Am. Chem. Soc.* 115:1705–1711 [1993]; Muñoz et al., *J. Chem. Soc. Chem. Commun.* 520–522 [1992]; Fyles and Zeng, *Chem. Commun.* 2295–2296 [1996]). The term "bola-amphiphiles" was first termed by Fuhrhop et al. to refer to several hydrophobic derivatives of succinic acid in which two polar headgroups are linked covalently by a hydrophobic, saturated hydrocarbon skeleton. (Fuhrhop et al., *Advances in Supramolecular Chemistry* Volume 2, Gokel, ed., pp. 25–63). Bola-amphiphiles often remain extended when dispersed in water and form monolayer lipid membrane vesicles known as bola-amphisomes. However, the bola-amphiphiles described by Muñoz are themselves used as building blocks of liposomes. As such, they are immobile and do not serve as carriers for the transport of molecules. Although their crown ether appendices are capable for transport of metal ions, these crown ethers are unable to transport zwitterions.

Thus, there remains a need in the art for development of carriers that can recognize and transport common aminoacids as zwitterions, as well as specific physiologically important molecules, such as catecholamines and neurotransmitters (i.e., γ-aminobutyric acid, serotonin noradrenaline, etc.). In addition, there remains a need in the art for the development of carriers that can be incorporated within liposome membranes for use in drug delivery systems.

SUMMARY OF THE INVENTION

The present invention relates to the development of carriers that are capable of interacting at more than one site and are effective in transporting zwitterions and other biologically important molecules. In particular, the present invention relates to ditopic receptor molecules that contain salicylaldimine and crown ether subunits, and complexed to metal ions.

In one embodiment, the present invention contemplates a compound, comprising first and second chelating groups linked via a linker group, said first chelating group comprising a crown ether, said second chelating group comprising a metal complexed to a macrocycle, wherein said compound is capable of transporting one or more amino acids or amino acid derivatives at a flux greater than $5 \times 10^{-3}$ mol/m$^2$-sec·mol$_{carrier}$ (and more preferably at a flux greater than 5×10$^{-3}$ mol/m$^2$-sec·mol$_{carrier}$. It is preferred that the above-specified compound is part of a transport system comprising the compound contained within a liposome.

Furthermore, the present invention carries a net positive charge and is obtained as a salt with halide ions as counterions. In preferred embodiments, the counterions are halides selected from the group consisting of chloride, bromide, and iodide ions.

It is not intended that the present invention be limited to a particular linker group. A variety of linker groups are contemplated. In one embodiment, said linker comprises a phenyl bridge.

It is also not intended that the present invention be limited by the nature of the macrocycle. In one embodiment, the macrocycle is modified with hydrophobic groups. In a preferred embodiment, the macrocycle comprises salicylaldimine modified with hydrophobic groups. In this regard, a variety of hydrophobic groups can be employed with success, including but not limited to tertiary butyl groups. A preferred modified salicylaldimine is 4,5-di(3,5-ditertiarybutylsalicylaldimine).

It is also not intended that the present invention be limited to a specific crown ether. However, a preferred crown ether is 18-benzo-crown-6.

Importantly, both the crown ether and the macrocycle are capable of binding metal ions, such as (for the macrocycle) manganese(III), nickel(II), cobalt(II), copper(II) and iron (III). In one embodiment, the crown ether is complexed with alkali cations, including but not limited to potassium and cesium.

It is not intended that the present invention be limited to the transport of just any particular amino acid or amino acid derivative. However, a preferred compound is capable of transporting dopamine at a flux greater than 5×10$^{-3}$ mol/m$^2$-sec·mol$_{carrier}$.

The present invention contemplates the synthesis of such compounds (as set forth below). Moreover, the present invention contemplates the use of such compounds in a variety of contexts and thus contemplates methods whereby the compounds of the present invention are employed (e.g., as sensors, separation resins, affinity resins, etc.).

DEFINITIONS

Figure 1:
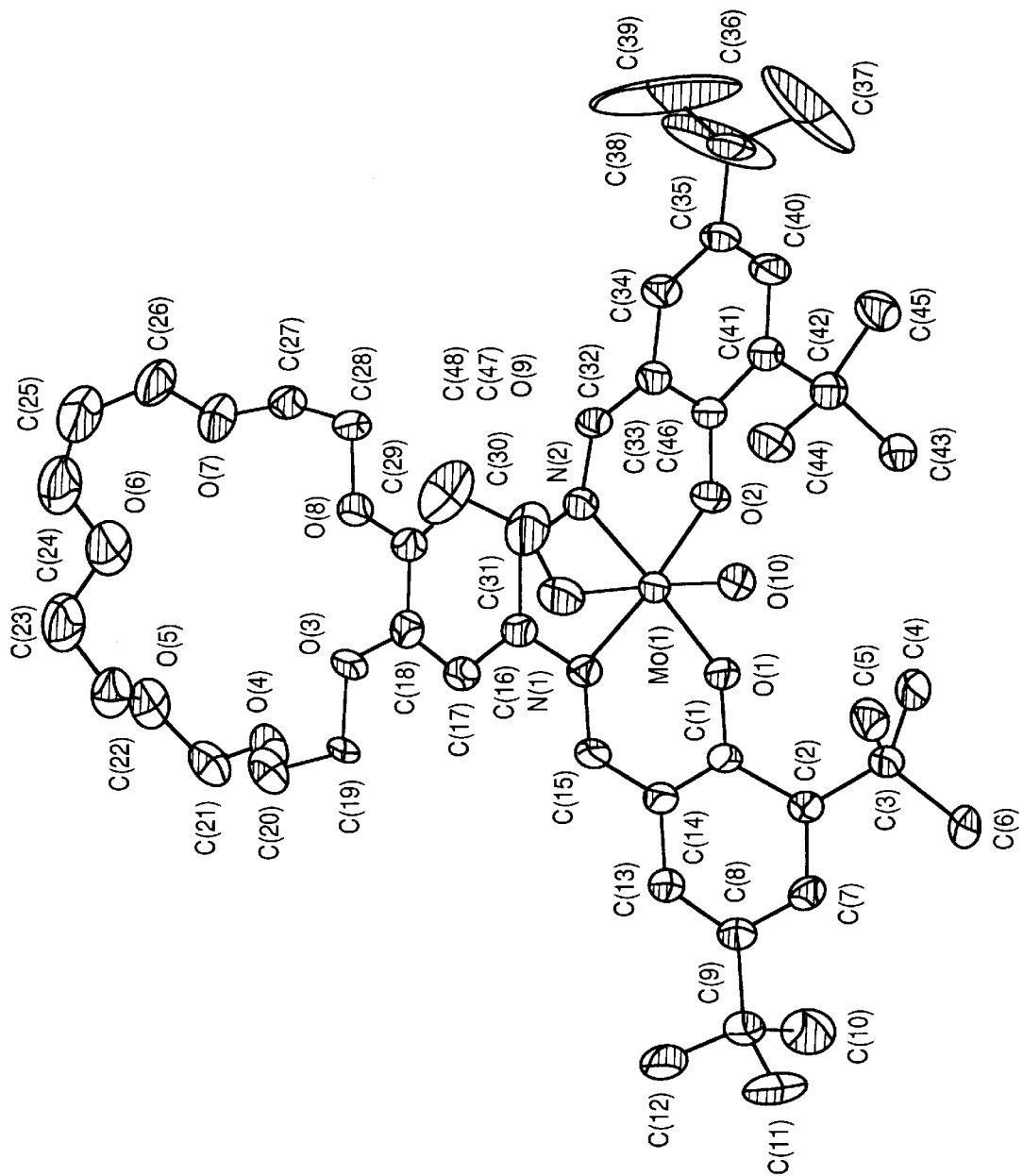
FIG. 1 shows the structure of chloro-manganese(III)-4,5-di(3,5-ditertiarybutylsalicylideneimine)benzo-18-crown-6.

The present invention relates to crown-ether functionalized metal salicylaldimine complexes are carriers for zwitterions. To facilitate understanding of the invention, a number of terms are defined below.

The term "crown ether" refers to a cyclic molecule in which ether groups (i.e., polyethers) are connected by dimethylene linkages.

The terms "complex," "complex compound" or "coordination compound" refer to a compound formed by the union of a metal ion, usually a transition metal, with a non-metallic ion or molecule called a ligand. The ligand may either be positively (i.e., NH$_2$NH$_3^+$) or negatively charged (i.e., Cl$^-$), or it may be a neutral molecule (i.e., water or ammonia).

The terms "ligand" "chelating group" or "complexing agent" refer to any molecule or molecular group that binds to a metal ion so as to form a coordination compound, a chelate, or other complex. Examples of chelating groups include (but are not limited to) crown ethers, salicylaldimine, ammonia, chlorine, ethylenediaminetetraacetic acid (EDTA), etc.

The term "chelate" refers to the type of coordination compound in which a central metal ion (i.e., Co$^{2+}$, Ni$^{2+}$ or Cu$^{2+}$) is attached by coordinate links to two or more nonmetal atoms (i.e., the ligands) in the same molecule.

The terms "macrocycle" or "macrocylic" refer to an organic molecule with a large ring structure containing over fifteen carbon atoms.

The term "host-guest" or "guest-host" refer to interactions between molecules that can enclose ions or atoms within their structure (i.e., "host"), and ions or atoms that are enclosed (i.e., "guest") without the normal chemical bonding.

The term "linker" refers to a molecule, molecular group or compound that serves as a bridge of attachment between two or more subunits of a molecule or between two or more functional groups.

The term "lipid" refers to a variety of compounds that are characterized by their solubility in organic solvents. Such compounds include, but are not limited to fats, waxes, steroids, sterols, glycolipids, glycosphingolipids (including gangliosides), phospholipids, terpenes, fat-soluble vitamins, prostaglandins, carotenes, and chlorophylls.

The term "liposomes" refers to artificially produced spherical lipid complexes that can be induced to segregate out of aqueous media.

The term "amino acid" refers to an organic acid containing both a basic amino group (NH$_2$) and an acidic carboxyl group (COOH). The term "amino acid derivative" refers to a molecule that contains either an amino group or a carboxyl group, said derivative capable of being chemically or enzymatically derived from an amino acid. For example, dopamine and norepinephrine are amino acid derivatives created from the conversion of L-tyrosine.

The term "zwitterion" refers to the amino acids that exist with equally ionized positive and negative groups.

The term "isoelectric point" refers to the pH at which the net charge on a molecule in solution is zero. At this pH, amino acids exist almost entirely in the zwitterion state.

The term "ion" refers to an atom, radical, molecule or a compound that has lost or gained one or more electrons, resulting in an electric charge. Positively charged ions are cations and negatively charged ions are anions.

The term "solvent" refers to a liquid compound that is used to dissolve solids, liquids, or gases without reacting with them (unless desired) to bring the reaction components into close chemical proximity. Generally speaking, in a solution consisting of several components, the component present in excess is deemed to be the solvent. Solvents are either polar (high dielectric constant) or nonpolar (low dielectric constant).

The term "ambient condition" refers to the conditions of the surrounding environment (e.g., the temperature of the room or outdoor environment in which an experiment occurs).

The term "filtration" refers to the operation of separating suspended solids from a liquid by forcing the mixture through a porous barrier. Almost any water-insoluble, porous material having a reasonable degree of rigidity can serve as a filter. For example, Celite, silica gel, or Whatman filter paper are commonly used for filtration.

The term "crystallization" or "recrystallization" refers to a means of purifying materials by evaporation and solidification. The solid to be purified is dissolved in a solvent that is slowly evaporated to give purified crystals.

The term "membrane" refers to, in its broadest sense, a thin sheet or layer of material. It is intended that the term encompass all "biomembranes" (i.e., any organic membrane including, but not limited to, plasma membranes, nuclear membranes, organelle membranes, and synthetic membranes). Typically, membranes are composed of lipids, proteins, glycolipids, steroids, sterols and/or other components.

The term "flux" refers to the rate of flow or transfer of electricity, magnetism, water, heat, energy, etc., the term being used to denote the quantity that crosses a unit area of a given surface in a unit of time per mole of carrier.

DETAILED DESCRIPTION OF THE INVENTION

The presently claimed invention relates to carriers capable of efficient transport of amino acids, amino acid derivatives and other biologically important molecules such as catecholamines and neurotransmitters (i.e., γ-aminobutyric acid, serotonin, noradrenaline), using crown-ether functionalized metal functionalized planar multidentate complexes as carriers for transport. It is contemplated that the carriers of the presently claimed invention dissolve in liposome membranes.

In particular, the presently claimed invention relates to the syntheses and characterization of ditopic receptor molecules that contain salicylaldimine and crown ether subunits complexed to a metal ion. These molecules are connected via phenyl "bridges" to crown ether subunits. The combination of a metal complex subunit (with potential to interact with lone pairs of electrons) and a crown ether appendix (capable of serving as a hydrogen bond acceptor site) make these molecules ideally suited for the multisite (ditopic) recognition of guest molecules that have groups that can either donate electron pairs or form hydrogen bonds. In addition, the crown ether-salicylidene complexes of the presently claimed invention comprises tertiarybutyl groups on the salicylaldimine ligands, which makes these compounds soluble in non-polar organic solvents or lipids. Without the modification with tertiarybutyl groups or other appropriate substituent groups that contain more than 4 and up to 25 carbon atoms, the complexes are much less effective as transporting agents. Furthermore, these molecules carry a net positive charge and are obtained as salts. In one embodiment, the crown ether is complexed with alkali cations (i.e., $K^+$, $Cs^+$).

The crown ether-salicylaldimine complexes of the presently claimed invention are synergistic in molecular interactions, which make the recognition and transport of guest molecules possible. The combination of crown ether subunit with salicyladimine complexes results in significantly higher rates of transport exhibited by the supramolecules, compared to rates of transport of guests by either crown ether molecules or salicylaldimine as separate entities. The transport of zwitterions such as amino acids is thermodynamically driven and not dependent on $H^+$ concentration gradients, and is facilitated by the crown ethersalicylaldimine metal complexes of the presently claimed invention, which do not need $H^+$ gradients for transport.

It is contemplated that the crown ether-salicylaldimine metal complexes of the presently claimed invention be incorporated into polymeric supports for the production of substrate sensitive probes to be used as sensors, particularly for materials which interact with crown ether-salicylaldimine, such as dopamine and serotonin.

It is also contemplated that the crown ether-salicylaldimine metal complexes of the presently claimed invention be attached to chromatographic column supports, for the separation of molecules from mixtures by high pressure liquid chromatography (HPLC).

Furthermore, it is contemplated that the incorporation of a cyclohexyl group in place of the benzo group will give molecules that can exist in two different optical isomeric forms. Resolution of racemic mixtures containing these optical isomers will make available pure enantiomers of the supramolecular carriers that should be useful in the transport, separation or recognition of either of the two antipodes of a racemic mixture of molecules.

A. Crown-Ether Functionalized Salicyladimine Complexes

In one embodiment, the crown ether is chloro-manganese (III)-4,5-di(3,5-ditertiarybutylsalicylideneimine)benzo-18-crown-6 [Mn(III)—I—(H$_2$O)(EtOH)]$^+$Cl$^-$ complex and its alkali derivatives. This molecule belongs in a general class of hybrid [crown-MR$_n$salphen]complexes that combine the electron pair donor characteristics of the crown ether component with the metal-dependent electron pair acceptor properties of the R$_n$salphen-bound metal ions. In other embodiments, the crown ethers are the $K^+$ and $Cs^+$ adducts of [Mn(III)—I—(H$_2$O) (EtOH)]$^+$Cl$^-$. The reaction of [Mn(III)—I—(H$_2$O)(EtOH)]$^+$ Cl$^-$ with potassium iodide gives chloro-manganese(III)-4,5-di-(3,5-ditertiarybutylsalicylideneimine)(potassium benzo-18-crown-6-iodide) [K—Mn—I]. The reaction of [Mn(III)—I—(H2O)(EtOH)]$^+$Cl$^-$ with 1 eq cesium iodide, and addition of half equivalent of cesium iodide during recyrstallization gives bis[(iodo)-manganese(III)-4,5-di-(3,5-ditertiarybutylsalicylideneimine)(cesium benzo-18-crown-6-chloride). The reaction of [Mn(III)—I—(H$_2$O)(EtOH)]$^+$ Cl$^-$ with half equivalent cesium iodide, and addition of excess cesium iodide during recyrstallization gives iodo-manganese(III)-4,5-di(3,5-ditertiarybutylsalicylideneimine) (cesium benzo-18-crown-6-iodide).

Crystallography data show that [Mn(III)—I—(H$_2$O)(EtOH)]$^+$Cl$^-$ is triclinic, space group P1; a=10.9387(2)Å, b=14.3794(2)Å, c=18.4478(4)Å, α=104.958(1)°, β=104.245(1)°, γ=99.140(1)°, z=2. Refinement of the structure by least squares methods converged to an R1 value of 0.059. In this complex the Mn(III) ion is coordinated by the salphen unit in [Mn(III)—I—(H$_2$O)(EtOH)]$^{+Cl-}$ with distances of Mn—O=1.866(2), and 1.784(2)Å and Mn—N= 1.990, 1.992 Å. The Mn(III) ion is axially coordinated by a water molecule, Mn—O=2.289(3)Å and by an ethanol molecule, Mn—O=2.215(3)Å. The Cl⁻ anion is not bound directly to the Mn(III) ion, but is hydrogen bonded to the coordinated OH group of the ethanol molecule. The water molecule is also hydrogen bonded to three of the oxygen atoms of the crown ether unit of another molecule in an interaction that results in centrosymmetric dimers. The Mn bound ethanol ligand trans to the water ligand (Mn—$O_{eth}$= 2.215(3)Å) is hydrogen bonded to the Cl⁻ ion (Cl⁻)$_{eth}$=3.025 (4)Å; Mn—Cl=4.541(1)Å) which is also hydrogen bonded to an ethanol molecule of solvation (Cl—$O_{eth(s)}$=3.085(4) Å). The magnetic moment of [Mn(III)—I—(H₂O)(EtOH)]⁺ Cl⁻ ($\mu_{corr}^{eff}$=4.85 B.M. at 300 K) is typical for a high spin $d_4$ ion. The structure of [Mn(III)—I—(H₂O)(EtOH)]⁺Cl⁻ is shown in FIG. 1.

In another embodiment, the crown ether is nickel-4,5-di (3,5-ditertiarybutylsalicylideneimine)benzo-18-crown-6 [Ni—I] and its alkali derivatives. In other embodiments, the crown ethers are the K⁺, Cs⁺ and hexylammonium adducts of Ni—I. The reaction of 4,5-di(3,5-ditertiarybutylsalicylideneimine ligand (I) with nickel acetate gives crystalline Ni—I, which reacts with potassium chloride and potassium iodide to give the alkali derivatives potassium nickel-4,5-di(3,5-ditertiarybutyl-salicylideneimine)benzo-18-crown-6 chloride (K—Ni—I)$^{Cl-}$ and potassium nickel-4,5-di(3,5-ditertiarybutyl-salicylideneimine)benzo-18-crown-6 iodide (K—Ni—I)⁺I⁻ respectively. The reaction of Ni—I with cesium iodide in a 1:1 and 2:1 molar ratios gave crystalline cesium nickel-4,5-di(3,5-ditertiarybutylsalicylideneimine)benzo-18-crown-6 iodide (Cs—Ni—I)⁺I⁻ and cesium bis-nickel-4,5-di(3,5-ditertiarybutyl-salicylideneimine)benzo-18-crown-6 iodide [Cs(Ni—I)₂]⁺I⁻ respectively. Slow evaporation of an acetone solution of Ni—I that contained hexylammonium chloride gave crystals of nickel-4,5-di(3,5-ditertiarybutylsalicylideneimine)benzo-18-crown-6-n-hexylammonium chloride (Ni—I—HexNH₃)⁺C⁻.

Figure 2A:
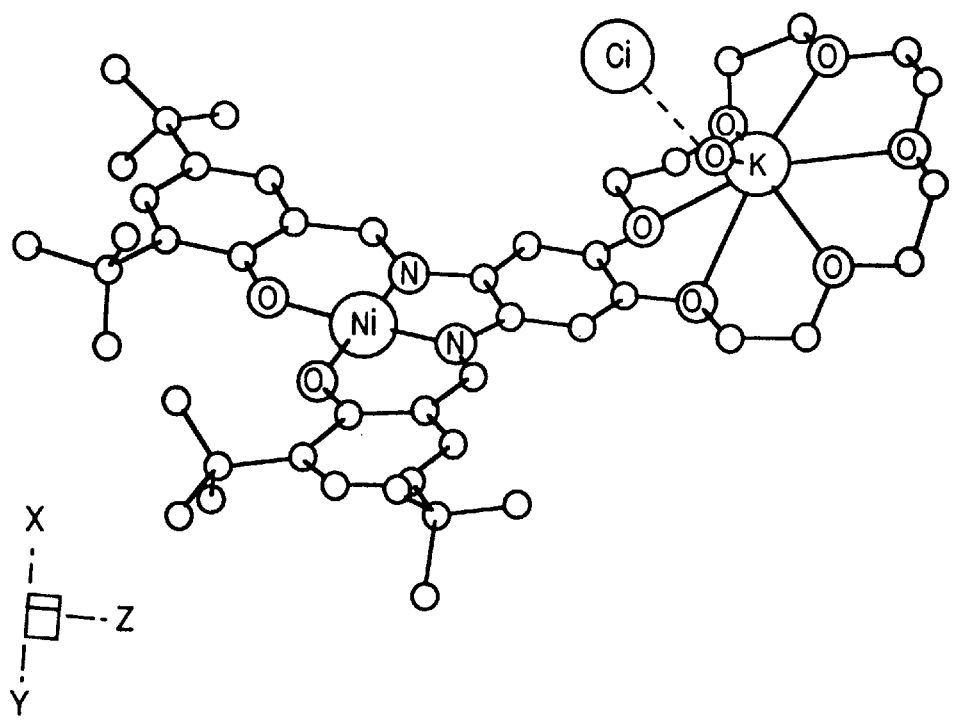
FIG. 2A shows the structure of potassium nickel 4,5-di(3,5-ditertiarybutylsalicylideneimine)benzo-18-crown-6.

The structures of (K—Ni—I)⁺Cl⁻, (Cs—Ni—I)⁺I⁻ and (Ni—I—HexNH₃)⁺Cl⁻ (FIG. 2) and of [Cs(Ni—I)₂]⁺I⁻ have been determined. In the monomeric (K—Ni—I)⁺Cl⁻ complex, the seven-coordinate K⁺ ion is bound to a water molecule (K—OH₂O=2.687(4)Å), in addition to the six crown-ether oxygen donors (K—O=2.83(2); Range 2.751 (4)Å–2.899(4)Å). The chloride anion is found at 3.478(1)Å from the K⁺ ion and 7.102(1)Å from the Ni⁺² ion, and is hydrogen bonded to the K⁺ bound water molecule at 3.409 (3)Å. Crystallography data show that [K—Ni—I—Cl·H₂O—CHCl₃] is triclinic, space group P1; a=10.379(1) Å, b=15.9553(2)Å, c=18.4490(3)Å, α=112.16(1)°, β=102.97(1)°, γ=96.43(1)°, z=2.

Figure 2B:
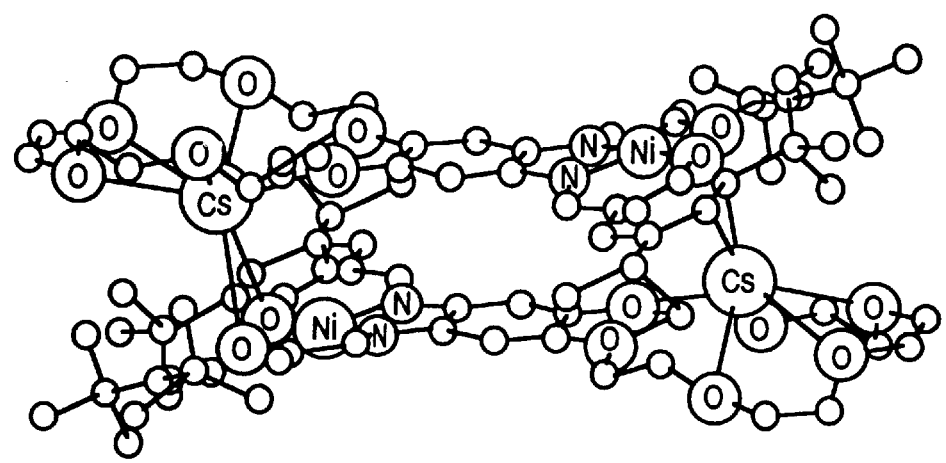
FIG. 2B shows the structure of cesium nickel 4,5-di(3,5-ditertiarybutylsalicylideneimine)benzo-18-crown-6.

The basic structural features of the Cs⁺ derivatives are determined by the coordination requirements of the large Cs⁺ ions that are coordinatively unsaturated when bound only by the oxygen donors of a single 18-crown-6 unit. This is the case with the (Cs—Ni—I)⁺I⁻ complex where the presence of one Cs⁺ ion per Ni—I results in dimer formation (Cs—Ni—I—I)₂ (FIG. 2B). In (Cs—Ni—I—I)₂, the Cs⁺ ions are eight coordinate. The Cs⁺ ions in each of the two Cs—Ni—I units, in addition to being coordinated by the 18-crown-6 moiety [(Cs—O=3.08(3)Å; range: 3.021(4)Å–3.177(4)Å)] also are coordinated by two salphen ligand oxygen atoms at 3.298 Å and 3.226 Å. The strength of these interactions becomes apparent in the appearance of a "parent" ion peak in the FAB⁺ mass spectrum of the compound at a mass of 1928, corresponding to the (Cs—Ni—I—I)₂ dimer. The I⁻ ion is found 7.246(4)Å from the Cs ion and close to five ligand carbon atoms at distances that range from 3.762(4)Å to 3.984(4)Å. An examination of the ¹H-NMR spectra of (Cs—Ni—I)⁺I⁻ shows that the dimer persists in CH₂Cl₂ but dissociates in DMSO solution. Crystallography data show that (Cs—Ni—I—I)₂ is triclinic, space group P1; a=10.06932(2)Å, b=16.6268(1)Å, c=19.23043(3)Å, α=114.672(1)°, β=102.098(1)°, γ=93.290(1)°, z=1.

Figure 2C:
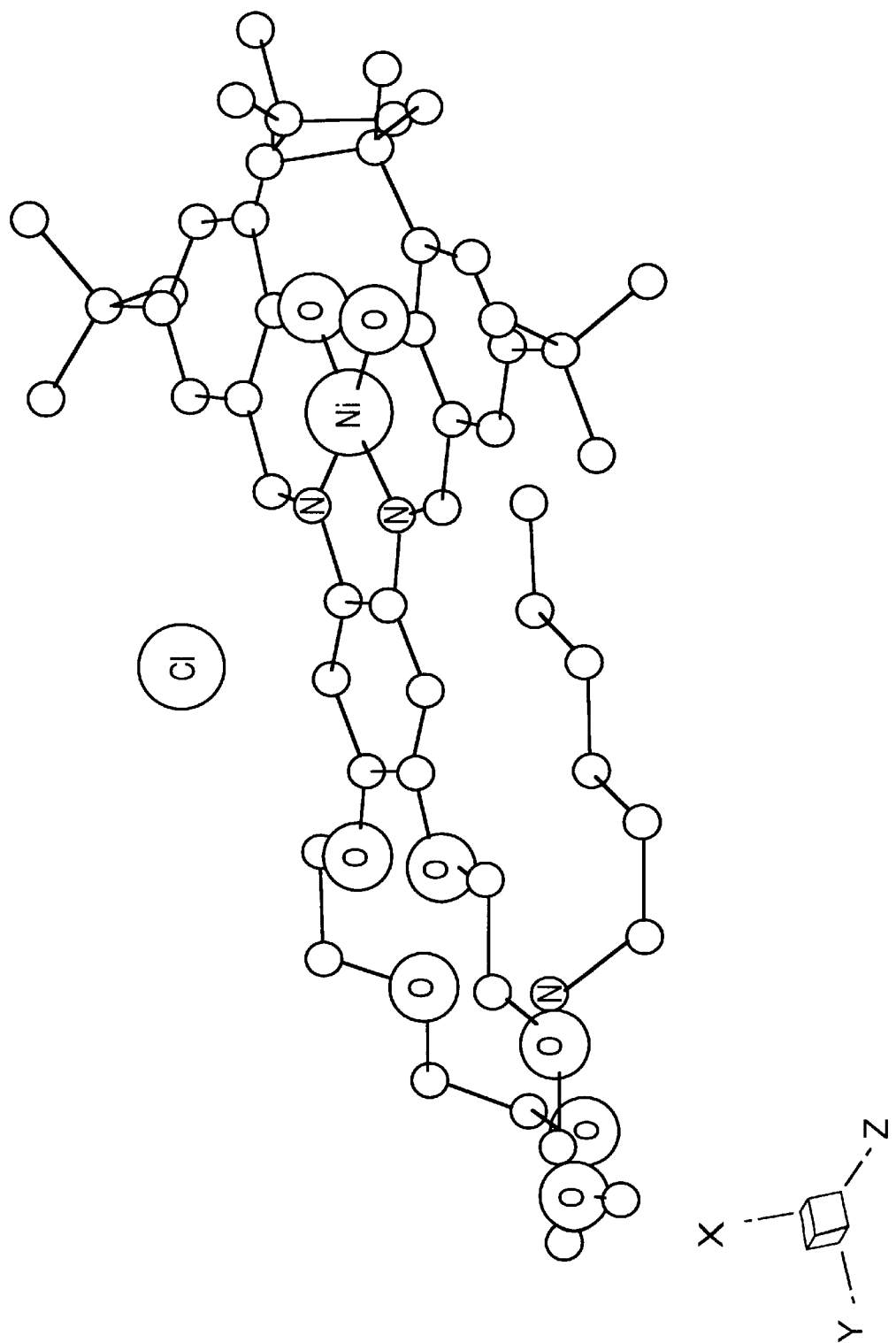
FIG. 2C shows the structure of nickel 4,5-di(3,5-ditertiarybutylsalicylideneimine)benzo-18-crown-6-n-hexylammonium chloride.

In the structure of the (Ni—I—HexNH₃)⁺Cl⁻ complex, the NH₃⁺ unit of the hexylammonium cation is located equidistant to all six oxygen atoms of the 18-crown-6 unit with an average N—O distance of 2.92(4)Å, which is indicative of strong H-bond interactions. The C₆ chain of the cation is nearly parallel to the salphen subunit at a distance of approximately 3.8 Å (FIG. 2C). Crystallography data show that (Ni—I—HexNH₃)⁺Cl⁻ is monoclinic, space group P2₁/n, a=10.5888(1)Å, b=19.1505(1)Å, c=30.0915(4) Å, β=93.714(1)°; z=4.

In [Cs—(Ni—I)₂⁺]I⁻, the Cs⁺ ion is twelve coordinate, and sandwiched between two 18-crown-6 units. Crystallography data show that [Cs-(Ni—I)₂⁺]I⁻ is triclinic, space group P1; a=18.818(4)Å, b=19.544(4)Å, c=20.334(4)Å, αc=106.57(3)°, β=102.75(3)°, γ=114.16(3), z=2. The refinement of the structures by full matrix least squares methods converged to R1 values of 0.060, 0.055, 0.12 and 0.056, respectively, for K—Ni—Cl·H₂O·CHCl₃, (Cs—Ni—I—I)₂, [Cs—(Ni—I)₂⁺]I⁻, and (Ni—I—HexNH₃)⁺Cl⁻.

In another embodiment, the crown ether is copper-4,5-di (3,5-ditertiarybutylsalicylideneimine)benzo-18-crown-6 [Cu—I] complex and its alkali derivatives. In yet another embodiment, the crown ether is cobalt 4,5-di(3,5-ditertiarybutylsalicylideneimine)benzo-18crown-6 [Co—I] complex and its alkali derivatives. In yet another embodiment, the crown ether is methoxy-iron(III) 4,5-di(3, 5-di-tertiarybutylsalicylideneimine)benzo-18-crown-6 [Fe—I] complex and its alkali derivatives. The reaction of 4,5-di(3,5-ditertiarybutylsalicylideneimine)benzo-18-crown-6 (I) with copper acetate and cobalt acetate gives copper4,5-di(3,5-ditertiarybutylsalicylideneimine)benzo-18-crown-6 [Cu—I] and cobalt 4,5-di(3,5-ditertiarybutylsalicylideneimine)benzo-18-crown-6 [Co—I] respectively. The reaction of potassium iodide with Cu—I and Co—I gives the potassium adducts copper-4,5-di(3,5-ditertiarybutylsalicylideneimine)potassium benzo-18-crown-6 and cobalt-4,5-di(3,5-ditertiarybutylsalicylideneimine)potassium benzo-18-crown-6, respectively. The reaction of I with iron(III) chloride, and addition of methanol gives methoxy-iron(III)-4,5-di(3,5-ditertiarybutylsalicylideneimine)benzo-18(Fe—I). The reaction of potassium chloride to Fe—I, and addition of potassium chloride during recrystallization gives methoxy-iron(III)4,5-di(3,5-ditertiarybutyl-salicylideneimine)potassium-benzo-18-crown-6-chloride. The reaction of Fe—I with LiOH gives ($\mu^2$-oxo)-bis[iron (III)-4,5-di(3,5-ditertiarybutylsalicylideneimine)benzo-18-crown-6)]. The reaction of ($\mu^2$-oxo)-bis[iron(III)-4,5-di(3,5-ditertiarybutyl- salicylideneimine)benzo-18-crown-6)] with potassium iodide and cesium iodide gives the alkali adducts ($\mu^2$-oxo)-bis[iron(III)-4,5-di(3,5-ditertiarybutylsalicylideneimine) potassium benzo-18-crown-6)iodide] and ($\mu^2$-oxo)-bis[iron(III)-4,5-di(3,5-ditertiarybutylsalicylideneimine)cesium benzo-18-crown-6) iodide] respectively.

B. Transport Properties

Figure 3:
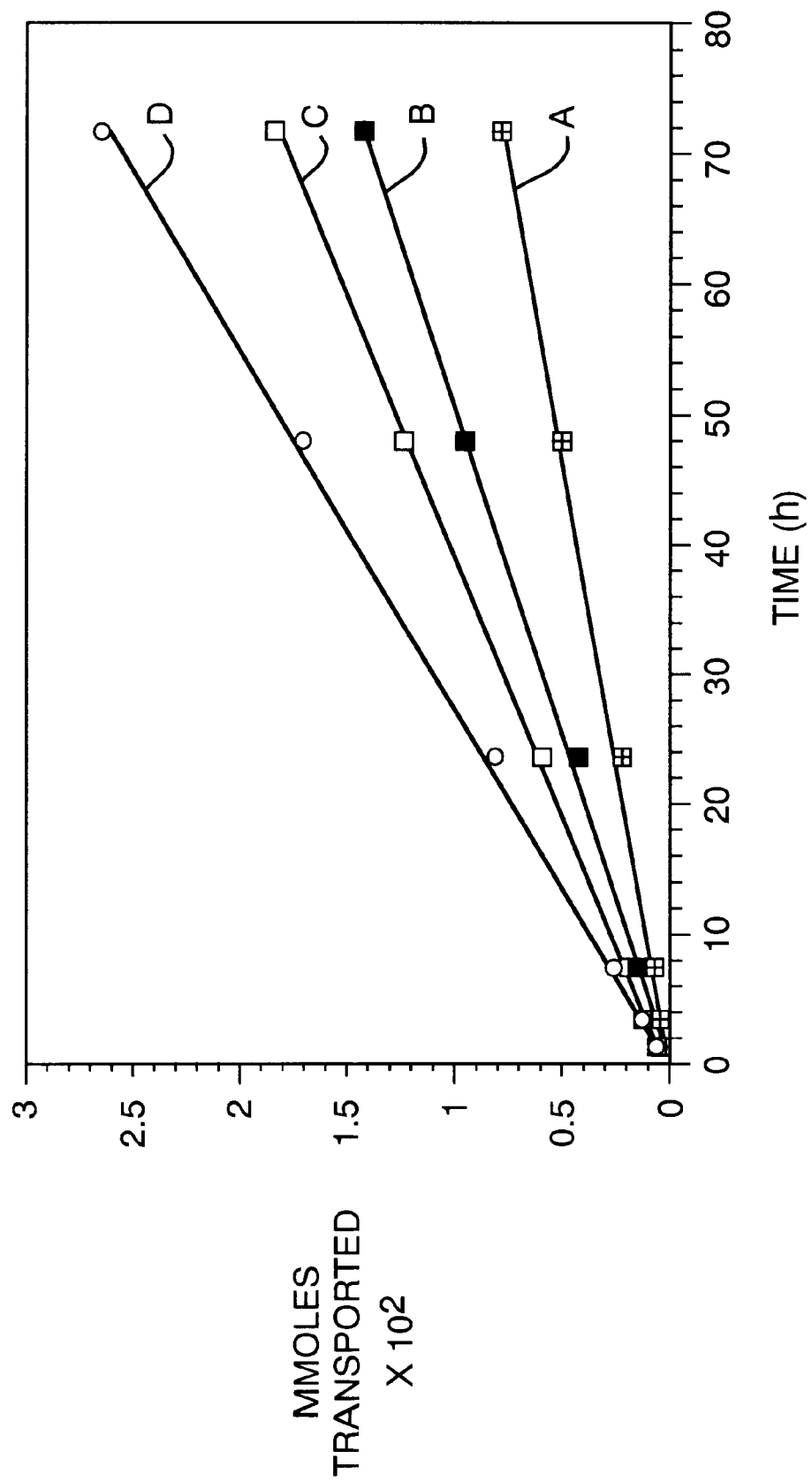
FIG. 3 shows the transport of tryptophan by nickel 4,5-di(3,5-ditertiarybutylsalicylideneimine)benzo-18-crown-6 and its alkali derivatives, compared with benzo-18-crown ether and its alkali derivatives.

The carrier properties of these molecules containing salicylaldimine and crown ether subunits have been investigated. Nickel 4,5-di(3,5-ditertiarybutylsalicylideneimine) benzo-18crown-6 (Ni—I) and their alkali metal ion derivatives show effective transport of aminoacids from acidic aqueous solutions to pure water. From an equimolar mixture of glycine, alanine, phenylalanine, histidine and tryptophan in aqueous solution (pH 2.7), the hydrophobic aminoacids (i.e., phenylalanine and tryptophan) are preferentially transported over the rest, which are either transported to a lesser extent or not at all. The transport of tryptophan from aqueous solution (isoelectric point, pH 5.89) using Ni—I, or its alkali metal derivatives as "carrier" molecules, however, was found nearly 50% slower than that observed for benzo-18crown-6 and the alkali metal ion loaded derivatives (FIG. 3). In this figure, A represents potassium nickel 4,5-di(3,5-ditertiarybutylsalicylideneimine)benzo-18-crown-6 [K—Ni—I]$^+$Cl$^-$; B represents nickel 4,5-di(3,5-ditertiarybutylsalicylideneimine)benzo-18-crown-6 [Ni—I]; C represents potassium benzo-18-crown-6 [K$^+$-Bz-18-crown-6]; and D represent Benzo-18crown-6. The initial transport rates for A, B, C, and D are $1.07(2)\times10^{-4}$ mmol h$^{-1}$, $2.00\times10^{-4}$ mmol h$^{-1}$, $2.51\times10^{-4}$ mmol h$^{-1}$ and $3.67\times10^{-4}$ mmol h$^{-1}$, respectively. The origin of this difference is difficult to ascertain but is very likely due to differences in the interface behavior and guest-host interactions for the different carrier molecules. For all carriers the rate of transport is slower in the presence of alkali metal ions. This inhibition undoubtedly is due to the competition between the aminoacid NH$_3^+$ group and the alkali metal ion for the 18crown-6 pocket. The Ni($^t$Bu$_4$salphen)-veratrol complex, which does not contain a crown ether group, is inactive in the transport of tryptophan. This result indicates that the transport properties of Ni—I are due entirely to the 18-crown-6 group, and the stability of the square planar Ni(II) site prevents coordination of the Ni(II) ion with moderately strong axial ligands and precludes its involvement as an electron accepting site in this molecule.

Figure 4:
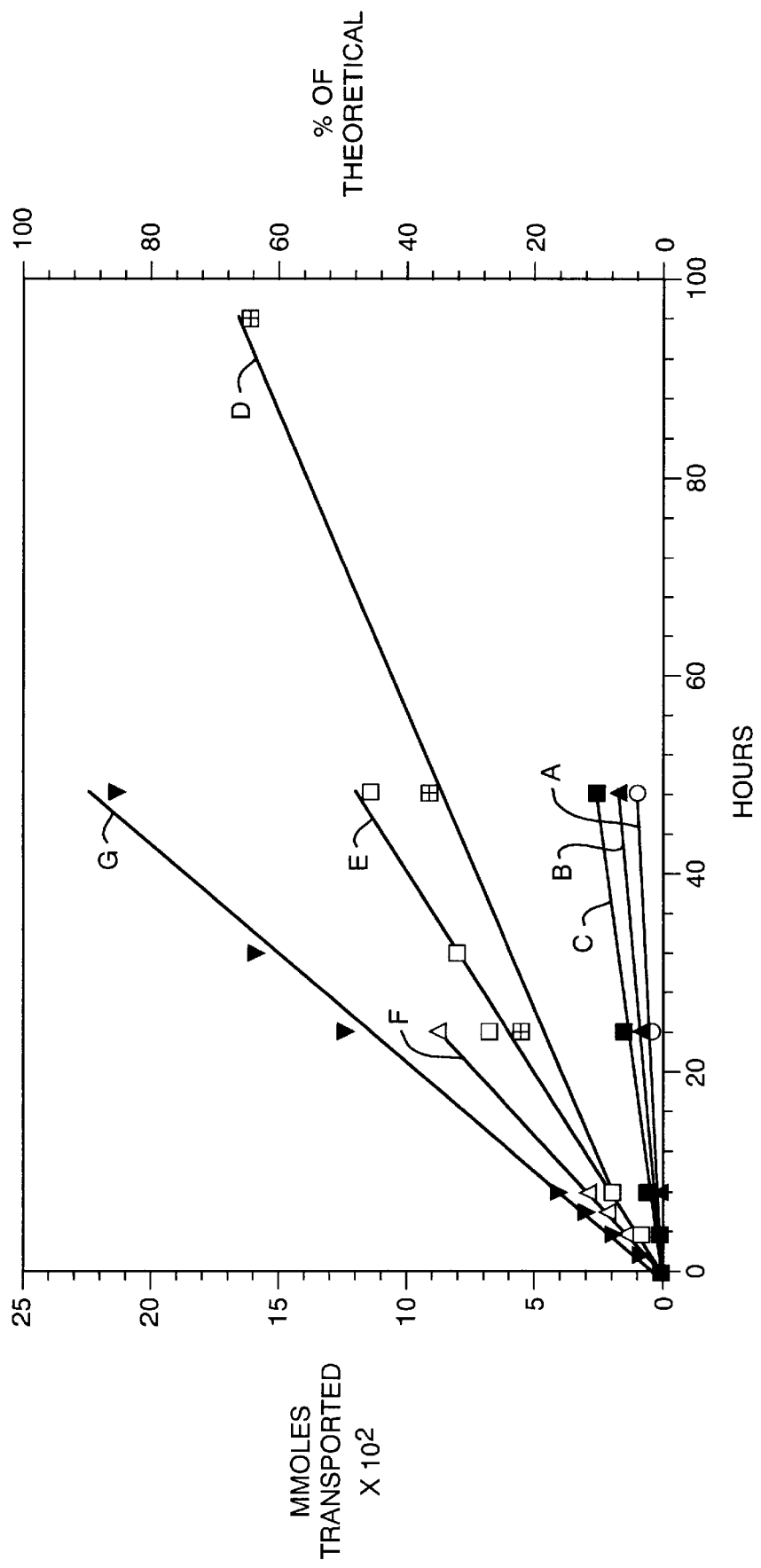
FIG. 4 shows the transport of tryptophan by chloro-manganese(III)-4,5-di(3,5-ditertiarybutylsalicylideneimine)benzo-18-crown-6 and its alkali derivatives, compared with nickel 4,5-di(3,5-ditertiarybutylsalicylideneimine)benzo-18-crown-6 and benzo-8-crown ethers and their alkali derivatives.
Figure 5A:
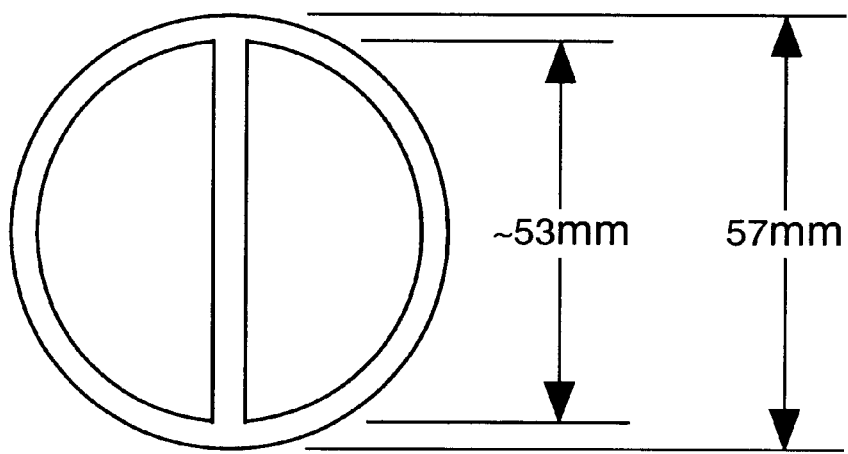
FIG. 5 shows the transport cell design used for transport studies.
Figure 5B:
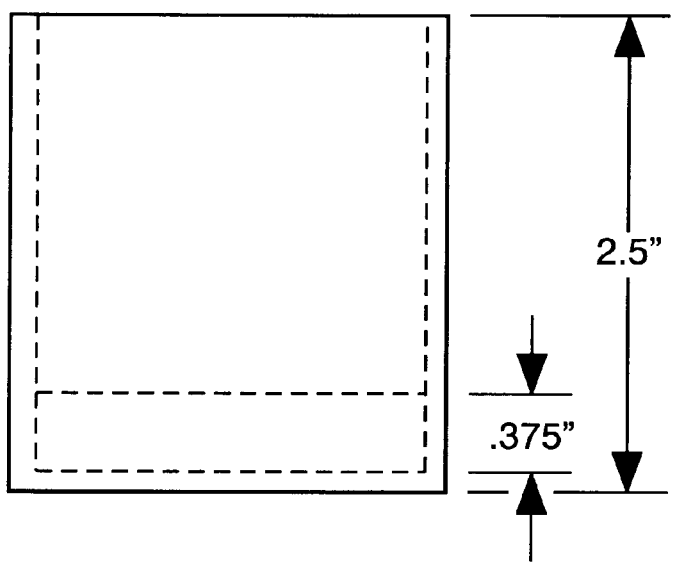

Chloro-manganese(III)-4,5-di(3,5-ditertiarybutylsalicylideneimine)benzo-18-crown-6 [Mn(III)—I—(H$_2$O)(EtOH)]$^+$Cl$^-$ complex and its alkali metal adducts (K$^+$, Cs$^+$) are effective in the transport of the aminoacid tryptophan from aqueous solution (isoelectric point, pH=5.89) between compartments separated by a CHCl$_3$ barrier membrane, and are superior to corresponding Ni(II) analog complexes (FIG. 4). In this figure, A is nickel-4,5-di(3,5-ditertiarysalicylideneimine)benzo-18-crown-6 (Ni—I); B is Benzo-18-crown-6; C is chloromanganese(III)-4,5-di(tertiarybutylsalicylideneimine)benzo-24-crown-8; D is chloromanganese(III)-4,5-di(tertiarybutylsalicylideneimine)benzo-18-6 [Mn(III)—I—(H$_2$O)(EtOH)]$^+$Cl$^-$; E is iodo-manganese(III)-4,5-di(tertiarybutylsalicylideneimine)potassium benzo-18-6-iodide [Cs—Mn—I]; F is chloro-manganese(III)-4,5-di(tertiarybutylsalicylideneimine)potassium benzo-18-6-iodide [K—Mn—I]; and G is bis[iodo-manganese(III)-4,5-di(tertiarybutylsalicylideneimine)potassium benzo-18-6-chloride] [Cs—Mn—(I)$_2$].

The slow rate of aminoacid transport observed with nickel-4,5-di(3,5-ditertiarysalicylideneimine)benzo-18-crown-6 (Ni—I) was comparable to that observed with simple benzo-18-crown-6. In the Ni—I complex, the Ni(II) site is inert to base adduct formation and very likely does not serve as an electron pair acceptor in the transport of guest molecules. This accounts for the similarity in transport properties between Ni—I and benzo-18-crown-6, which both contain the 18-crown-6 unit as the only guest binding site. Consistent with these observations is the inability of the Ni($^t$Bu$_4$salphen)-veratrol complex to facilitate transport of tryptophan. In Ni($^t$Bu$_4$salphen)-veratrol complex, the benzo-18-C-6 unit has been replaced by a 1,2-dimethoxy phenyl group (veratrol). In contrast, Mn($^t$Bu$_4$salphen)-veratrol complex, which does not contain a crown ether group, was found active in the transport of tryptophan, albeit at a slow rate and an initial flux value of $1.0\times10^{-2}$ mol/m$^2$-sec·mol$_{carrier}$. This value is comparable to that obtained for Ni—I at $2.0\times10^{-2}$ mol/m$^2$-sec·mol$_{carrier}$. The marginal transport properties of Mn($^t$Bu$_4$salphen)-veratrol complex must be attributed to the Mn(III) axial sites that can be made available for interactions with electron donors (possibly the carboxylate group of tryptophan). The sum of the initial fluxes of Ni—I and Mn($^t$Bu$_4$salphen)-veratrol complex falls short of that obtained for [Mn—I—(H$_2$O)(EtOH)]$^+$Cl$^-$ at $2.3\times10^{-5}$ mol/m$^2$s. These results suggest that in [Mn—I—(H$_2$O)(EtOH)]$^+$Cl$^-$, both the Mn(III) and the 18-crown-6 sites contribute to the transport of tryptophan in a synergistic rather than an additive fashion.

The transport rates of phenyl alanine, dopamine and serotonin ·HCl using [Mn—I—(H$_2$O)(EtOH)]$^+$Cl$^-$ as carrier were measured and initial flux values of $2\times10^{-2}$ mol/m$^2$-sec·mol$_{carrier}$, $2.2\times10^{-2}$ mol/m$^2$-sec·mol$_{carrier}$ and $2.7\times10^{-2}$ mol/m$^2$-sec·mol$_{carrier}$ were obtained, respectively. These values are an order of magnitude smaller than the flux obtained with the same carrier and tryptophan (FIG. 4–D), but 4–5 fold larger than values obtained with benzo-18-crown-6 as a carrier. For comparison, the initial flux for dopamine transport through a CHCl$_3$ bulk liquid membrane using the phenyl boronic acid-18-crown-6 system, has been reported to be $2\times10^{-3}$ mol/m$^2$-sec·mol$_{carrier}$ with a five-fold higher concentration of carrier. (Paugam et al., *J. Am. Chem. Soc.* 116:6124–6125).

The introduction of K$^+$ or Cs$^+$ in the crown-ether cavity of [Mn—I—(H$_2$O)(EtOH)]$^+$Cl$^-$ results in tryptophan transport rates even better than those shown by [Mn—I—(H$_2$O)(EtOH)]$^+$Cl$^-$ alone. This contrasts with the transport rates observed with the alkali metal derivatives of Ni—I which were found considerably slower than those of alkali-metal free Ni—I. Furthermore, the importance of the crown ether size in the transport process is underscored by the observation that the 24-crown-8 analog of [Mn—I—(H$_2$O)(EtOH)]$^+$Cl$^-$ (C, FIG. 4) is approximately four times slower than [Mn—I—(H$_2$O)(EtOH)]$^+$Cl$^-$.

Possible binding sites for the Lewis acid or Lewis base groups of guest molecules in [Mn—I—(H$_2$O)(EtOH)]$^+$Cl$^-$ include the Mn(III)-OH$_2$ center that can serve either as an electron pair acceptor (following dissociation of the kinetically labile H$_2$O ligand) or a hydrogen bond acceptor (via a coordinated H$_2$O molecule). The 18-crown-6 group may serve as a hydrogen bond accepting site but upon addition of an alkali metal ion (K$^+$, Cs$^+$) is converted to an electron pair acceptor. The bridging phenyl group also could serve as a π—π interaction site.

The transport of ω-amino-hexanoic acid was also examined and found to be considerably slower than that of tryptophan when complex [Mn—I—(H$_2$O)(EtOH)]$^+$Cl$^-$ was used as a carrier, but virtually non-detectable when complex benzo-18-crown-6 was used. The difference in the relative transport rates of tryptophan versus amino-hexanoic acid by [Mn—I—(H$_2$O) (EtOH)]$^+$Cl$^-$ may be a consequence of π—π interactions that are possible with [Mn—I—(H$_2$O)(EtOH)]$^+$Cl$^-$, but absent with complex benzo-crown-6.

C. Liposomes

As noted above, the present invention contemplates a transport system comprising the above-discussed compounds contained within a liposome. Liposomes are closed vesicles that enclose an internal aqueous space, with an internal compartment that is separated from the external medium by a bilayer membrane composed of discrete lipid molecules.

It is not intended that the present invention be limited to a particular type of liposome. Indeed, liposomes can vary in size, shape, and composition. Traditionally, the membrane components of liposomes have been phospholipids, particularly phosphatidyl cholines, partly because they are the building blocks that nature itself uses to form membranes, and partly because the common phospholipids are lamella-forming lipids under all conditions and can do so easily without the aid of additional components. Recently, bilayer membrane vesicles have been constructed using single-chain amphiphiles (e.g., UFAsomes) or non-ionic surfactants in which the principles of formation and physical properties are similar to conventional liposomes.

Liposomes also include those where the "bilayer" membrane is composed of membrane-spanning lipids in which the membrane components are long lipidic chains with polar moieties at either end. In theory, each molecule has one polar group at the internal surface of the membrane and the other at the external face. Liposomal membrane compounds can also be chemically linked to each other by polymerization, to form an extensive network of interlinked macromolecules. To form these structures, however, a conventional liposome is first constructed from individual monomer units making up a fluid membrane. The chemical cross-linking may be thought of as a natural extension of the non-covalent interactions between membrane components (i.e., van der Waals, hydrogen bonding, electrostatic), which are essential for maintaining stability of the membrane in the first place. Finally, liposomes can also be the single cell.

Different types of liposomes can also be described under certain distinguishing characteristics such as size, morphology, method of preparation, and chemical composition or behavior in biological systems. A variety of such liposomes contemplated by the present invention is discussed below.

1. Liposomes Categorized By Size
  i. Small unilamellar vesicle (SUV)

This term refers to single-shelled vesicles produced as a result of high-intensity (probe) ultrasonication, and the abbreviation may thus also be considered to stand for "sonicated unilamellar vesicles." The liposomes prepared by this method are of the limit size, i.e., the smallest possible size that curvature of bilayer membranes will permit on steric grounds. At present, ultrasonication, which may be used together with certain high-pressure extrusion techniques and the alcohol injection method of Batzri and Korn, is the only method that is capable of giving vesicles in this smallest size range. Because the SUVs approach the "limit size" in diameter, SUVs are a population of liposomes more homogenous in size than liposomes prepared by other methods. Subsequently, because of the high energy imparted by ultrasonication and the constraints in packing resulting from forcing the membrane to adopt to a high degree of curvature, SUVs are a rather unusual type of liposome, and demonstrate many properties atypical of liposomes in general.

ii. Large unilamellar vesicle (LUV)

This term refers to single-shelled vesicles of diameters greater than that of SUVs, with differing definitions as to what constitutes "large" in this context. The first methods developed to prepare such vesicles were calcium-induced fusion of liposomes composed of SUVs, and ether injection, i.e., introduction of ether solutions of PC into hot aqueous buffer to form large planar sheets of bilayer membrane that fold in on themselves. Liposomes produced by these methods are of the order of 0.5 pm in diameter. However, the term LUV has been used in reference to any unilamellar vesicle larger than an SUV.

iii. Intermediate-sized unilamellar vesicle (IUV)

This term refers to liposomes within the 100 to 200- nm region between SUVs (25 nm) and LUVs (500 nm). Liposomes of this size are easily prepared by high-pressure extrusion or by detergent dialysis and are important in pharmaceutical applications since they fit into a size window that displays longer circulation times in the bloodstream, good stability, and ease of sterilization by membrane filtration. Other types of large liposomes described in published works are "cell-size" liposomes, and "giant" liposomes, referring to vesicles of many microns in diameter.

2. Liposomes Categorized By Morphology
  i. Multilamellar vesicle (MLV)

This term refers liposomes of any size that are composed of more than one bilayer membrane. Since even a liposome of just two bilayers is at least twice the size of an SUV, MLVs are readily distinguishable from SUVs in terms of size. MLVs are easily formed, and obtainable by gentle manual shaking of dry phospholipids in water. The lamellarity of these MLVs depends on lipid composition among other factors, but it typically varies between 5 and 20 bilayers. Liposomes with lower numbers of lamellae are sometimes referred to as oligo-lamellar or pauci-lamellar liposomes, although acronyms have not been adopted for these terms.

ii. Multivesicular Liposome (MVL)

This type of liposome is bound by an external bilayer membrane shell. A double emulsion is formed (water-in-oil) in which multiple aqueous droplets are suspended within single droplets of organic solvent, with phospholipids forming monolayers at both the external and internal oil-water interfaces. Removal of the organic solvent gives a particle composed of numerous distinct compartments distributed throughout the interior, separated from each other by single bilayer membranes. Topologically, each internal compartment is equivalent to every other, in contrast to the different compartments within conventional MLV, in which the separate aqueous compartments are all located concentrically within the vesicle. The unusual structure of MLVs necessitates junctions in two or three dimensions in which three or four different membrane sheets come together. To stabilize this configuration it appears that inclusion of neutral, non-bilayer-forming lipids in the membrane may be advantageous. The presence of internal membranes distributed as a network throughout MVLs may also serve to confer increased mechanical strength to the vesicle, while still maintaining a high volume:lipid ratio compared with MLVs. The multivesicular nature also indicates that, unlike LUVs, a single breach in the external membrane will not result in total release of the internal aqueous contents, giving rise to additional stability in vitro and in vivo.

iii. Stable plurilamellar vesicle (SPLV)

This term refers to liposomes manufactured by a special process that results in the entrapped solute being evenly distributed throughout the entire vesicle. This appears to be something that is not always achieved by conventional methods for preparation of MLVs, which give rise to osmotic differences between internal compartments that leave the intervening membranes in a stressed (and therefore unstable) condition. In the SPLV method, bath sonication during removal of solvent from a water-in-oil emulsion consisting of an ethereal PC solution relieves this stress.

3. Method of Preparation
  i. Large unilamellar vesicle by extrusion technology (LUVET)

Extrusion of liposomes through porous membranes was developed as a method of modifying their size. In this method, liposomes break down as they pass through porous membranes, resulting in liposomes with an upper size limit closely approximating that of the pores of the membrane themselves. At relatively low pressures (100 p.s.i), MLVs retain their multilamellar characteristics, while displaying a reduced-size heterogeneity. At higher pressures, however, the higher shear forces resulting from the greater pressure differential across the membrane filter result in reorganizations of the phospholipid bilayers giving rise to unilamellar vesicles, which are termed LUVETs. Repetition of the process several times again leads to a population with an upper size limit determined by the pore size of the membrane.

ii. Reverse-phase evaporation vesicle (REV)

The key feature of the preparation method for this type of liposome is the formation of a water-in-oil dispersion (i.e., a reverse-phase emulsion) from which the organic phase (usually an ether) is evaporated off. The result is a gel consisting of aqueous vesicles bound by a single monolayer of phospholipid. Mechanical agitation ruptures a proportion of the vesicles, and the phospholipid released provides the outer monolayer to convert the remaining vesicles into large unilamellar bilayer liposomes.

iii. Dehydration-rehydration vesicle (DRV)

In this type of vesicle, a process of dehydration followed by rehydration has been employed to entrap material inside the liposomes. The starting point is a suspension of empty SUVs, to which the solute to be entrapped is added, such that the solute is outside the liposomes in the external medium. Lyophilization of the mixture, followed by subsequent readdition of a limited volume of water brings about reorganization of the lipid membranes such that after fusion they reform liposomes in which a considerable proportion of the aqueous solute is now located within the vesicles. The liposomes obtained are somewhat larger than the original SUVs started with. Entrapments greater than 50% can be achieved. Because the energy to which the lipids are subjected is imparted in the absence of the solute (which is added only after formation of the SUVs), the method is good for the entrapment of sensitive molecules such as proteins.

4. Liposome Composition i. Proteosomes

Proteosomes are lipid vesicles incorporating proteins in or on the outer membrane.

ii. Immunoliposomes

This term refers to liposomes that use immunological molecules, particularly immunoglobulins for targeting purposes. Like other proteins, immunoglobulins may be attached to the liposome surface by covalent linkage through membrane lipids possessing functional groups. In certain circumstances, the proteins may be conjugated to free lipids, and the whole conjugate incorporated into the membrane during formation of the liposome. Since immunoliposomes incorporate proteins, they are also proteosomes. It is further noted that immunoliposomes are not liposomes that elicit an immune response.

5. Liposome Function i. Stealth

This term refers to any liposome that avoids uptake by the RES (and hence has a long circulation in the bloodstream) as a result of coating the liposomes surface with hydroxylated polymers. Two approaches have been identified to achieve this aim: in one case a combination of sphingomyelin and gangliosides (e.g., oligosaccharide-containing ceramides) are incorporated directly into the membrane. In the second approach, polyethylene glycol chains are conjugated to the surface. Optimal molecular weight of the chains is 2000.

ii. Transfersomes

This term refers to a liposome of a particular composition that has been demonstrated to be capable of transferring aqueous contents across the skin. The important features of the liposomes are that the membrane contains a certain proportion of bile salt distributed among the phospholipid, which confers markedly increased flexibility on the membrane, and that the liposome adopts a configuration in which the internal volume is insufficient to inflate the external membrane fully, so that it is flaccid and readily deformable. Such liposomes are capable of being extruded through narrow channels without rupture and can be driven across the skin barrier under the influence of an osmotic potential difference.

EXPERIMENTAL

The following examples are provided in order to demonstrate and further illustrate certain preferred embodiments and aspects of the present invention and are not to be construed as limiting the scope thereof. Although embodiments have been described with some particularity, many modifications and variations of the preferred embodiment are possible without deviating from the invention.

In the experimental disclosure which follows, the following abbreviations apply: $N_2$ (nitrogen); $CH_3OH$ (methanol); $CH_3CH_2OH$ (ethanol); $CH_2Cl_2$ (methylene chloride); $H_2O$ (water); KI (potassium iodide); CsI (cesium iodide); DMSO (dimethylsulfoxide); DMSO-$d_6$ (deuterated dimethylsulfoxide); $CHCl_3$ (chloroform); $NH_3$ (ammonia); $MnCl_2$ (manganese chloride); EtOH (ethanol); $HNO_3$ (nitric acid); HCl (hydrogen chloride); $CH_3CN$ (acetonitrile); $CD_2Cl_2$ (deuterated methylene chloride); K (potassium); $K^+$(potassium cation); Cs (cesium); $Cs^+$ (cesium cation); Ni (nickel); Mn (manganese); Cl (chlorine); $Cl^-$ (chloride anion); O (oxygen); C (carbon); H (hydrogen); N (nitrogen); $tBu_4$salphen [4,5-di(3,5-ditertiarybutylsalicylideneimine) ligand]; Å (Angstrom); $\mu$ (magnetic moment); s or sec (seconds); h or hr (hours); M (molar); mol (moles); mmol (millimoles); mM (millimolar); nm (nanometer); M% (mole percent); g (grams); mg (milligrams); $\mu$g (micrograms); 1 or L (liters); mL (milliliters); cm (centimeters); $cm^{-1}$ (wavenumbers); °C. (degrees Centigrade); $cm^2$ (square centimeter); $m^2$ (square meter); $M^{-1} cm^{-1}$ (absorbance); $\epsilon$ (extinction coefficient); mol/$m^2$·sec·mol$_{carrier}$ (rate of reaction); NMR (Nuclear Magnetic Resonance); ppm (parts per million); TMS (tetramethylsilane); MHz (megahertz); $\delta$ (chemical shift); J (coupling constant); s (singlet); d (doublet); t (triplet); q (quartet); m (multiplet); I.R. (Infrared Spectroscopy); far-I.R. (far-infrared Spectroscopy); vs (very strong); s (strong); m (medium); w (weak); vw (very weak); v (variable); mp (melting point); UV-Vis (ultraviolet-visible spectra); sh (shoulder); br (broad); M.S. (mass spectrometry); m/e (mass-to-charge ratio); FAB (fast atom bombardment); 3-NBA (3-nitrobenzyl alcohol); EI (electron ionization); eV (electron volts); m.p. (melting point); eq (equivalents).

Unless otherwise indicated, all chemicals and reagents were obtained from commercially available sources, such as Sigma and Aldrich. Solvents were purchased from Aldrich and most were used without further purification. For procedures requiring dry solvent, the solvent was distilled from an appropriate drying agent. Methanol was distilled from anhydrous magnesium sulfate. Acetone was distilled from Drierite$^R$. Ether was distilled from sodium-benzophenone. Hexanes was distilled from calcium hydride. N,N'-dimethylformamide was distilled from calcium hydride, and stored over molecular sieves. Pyridine was distilled from sodium hydroxide and stored over molecular sieves. Acetonitrile was distilled from anhydrous boron hydride and stored over molecular sieves. Molecular sieves (3A, 4–8 mesh) were purchased from Aldrich and activated in a furnace at 450–500° C. for 48 hours before using. Sieves are stored under prepurified nitrogen prior to use.

Medium range infrared spectroscopy (I.R.) was recorded using a Nicolet DX V4.56 spectrometer and far-infrared spectroscopy (Far-I.R.) was recorded using a Nicolet 740 FT-IT spectrometer. Samples were scanned in either a potassium bromide (KBr) or cesium iodide (CsI) disk. Ultraviolet-visible spectra (UV-Vis) were recorded on a Varian CARY 1E UV-Visible spectrometer using baseline correction for the solvent and a single measurement of about 0.5 to 1 mM in a 1 mm cell. $^1$H NMR spectra were recorded on a Bruker FX 300 or 360 MHz pulse FT-NMR instrument and the solvent was used as an internal reference for all compounds. Magnetics data were recorded from 300 K to 4K on an MPMS squid magnetometer and in all cases are reported per mole. Mass spectroscopy (M.S.) was determined using electron impact via direct inlet or positive-ion fast atom bombardment (FAB) with 3-nitrobenzyl alcohol (3-NBA) as a matrix where indicated.

EXAMPLE 1

Preparation of 4,5-diaminobenzo-18-crown-6

An amount of benzo-8-crown-6 (16.0 mmol, 5 g) was slowly added as a solid over thirty minutes to concentrated nitric acid (150 mL) with stirring. The solution became yellow and stirred at room temperature until all remaining solids dissolved. To this solution was added chloroform (100 mL). The reaction mixture was stirred continually for seven days. After this time, the acid was diluted with an equal volume of distilled water. The organic mixture was extracted with three portions of chloroform (100 mL). Solvent evaporation gave a yellow waxy residue of 4,5-dinitrobenzo-18-crown-6 in 85% yield, which was used without further purification. $^1$H NMR [In DMSO-$d_6$, 300 MHz, ppm] Aromatic protons δ=7.760 (s, 2H); Crown protons δ=4.300 (m, 4H), 3.766 (m, 4H), 3.760 (m, 4H), 3.550 (m, 4H), 3.497 (s, 4H).

An amount of 4,5-dinitro-18-crown-6 (4.95 mmol, 2 g) was ground to a fine powder and placed into a hydrogenation vessel along with palladium (1 g) on activated carbon (5%), and distilled methanol (100 mL). The mixture was degassed and allowed to react with hydrogen gas at about 40 p.s.i. with agitation for 18 hours. The solution was filtered under Schlenk conditions through a minimal pad of Celite. The solvent was removed using a cold trap to give a pale off-white powder of 4,5-diaminobenzo-18-crown-6 in 50% yield. The pale off-white powder obtained readily decomposes in solution when exposed to air, and moderately stable as a solid. In all cases, it was stored under nitrogen in a sealed container, inside a glove box, and used as soon as possible.

EXAMPLE 2

Preparation of 4,5-di(3,5-ditertiarybutylsalicylideneimine)benzo-18-crown-6

(I)

In an inert atmosphere, an amount of 4,5 diamino-benzo-18-crown-6 (2.91 mmol, 1 g) and 3,5-ditertiarybutylsalicylaldehyde (5.82 mmol, 1.36 g), were placed in distilled, degassed methanol (50 mL). The reaction vessel was removed from the atmosphere, purged with $N_2$ gas and the solution was refluxed with stirring under $N_2$ overnight. The product precipitated from solution upon cooling as a yellow powder, and was isolated by filtration in air to give 3.25 g (72% yield) of 4,5-di(3,5-ditertiarybutylsalicylideneimine)benzo-18-crown-6 ligand. M.p.=95–100° C. Analysis: Calculated for ($C_{46}H_{66}N_2O_8$+$H_2O$)(MW=793): C, 69.67; H, 8.64; N, 3.53. Found: C, 69.66; H, 8.58; N, 3.57. UV-Vis: (0.469 mM in $CH_3CN$) [nm (ε×10$^3$ $M^{-1}$ $cm^{-1}$)]: 392 (sh, 16.9), 355 (br, 23.0), 306 (sh, 16.2), 278(26.4), 239 (sh, 25.1). M.S.: [EI 70EV] Calculated (M—$H_2O$) m/e=775, found 774. I.R.: [CsI, $cm^{-1}$] 2959 (vs), 2910 (m), 2868 (m), 1614 (vs), 1577 (w), 1560 (w), 1540 (w), 1512 (s), 1466 (m), 1457 (m) 1438 (m), 1393 (w), 1361 (m), 1328 (w), 1268 (s), 1252 (s), 1233 (m), 1200 (s), 1173 (s), 1121 (m), 1059 (w), 1028 (w), 984 (w), 960 (m), 879 (w), 831 (w), 774 (w). $^1$H NMR [In $CD_2Cl_2$-$d_2$, 300MHz, ppm] Aromatic protons δ=8.675 (s, 2H), 7.427 (d, 2H, J=2.4 Hz), 7.252 (d, 2H, J=2.4 Hz), 6.853 (s, 2H); Crown protons δ=4.228 (m, 4H), 3.897 (m, 4), 3.711 (m, 4H), 3.667 (m, 4H), 3.630 (s, 4H); Tertiary butyl protons δ=1.425 (s, 18H); 1.318 (s, 18H). Water 1.56 (s). Hydroxy group 13.68 (s, 2H).

EXAMPLE 3

Preparation of Nickel-4,5-di(3,5-ditertiarybutylsalicylideneimine)benzo-18-crown-6
(Ni—I)

An amount of nickel acetate (0.646 mmol, 0.16 g) is dissolved in methanol (50 mL) and added to a solution of 4,5-di(3,5-ditertiarybutylsalicylideneimine)benzo-18-crown-6 ligand (0.646 mmol, 0.5 g) in $CH_2Cl_2$ (50 mL), resulting in an intense red color. The solid is recovered by evaporating off the solvent. Fibrous red crystals of nickel-4,5-di(3,5-ditertiarybutylsalicylideneimine)benzo-18-crown-6 was obtained in 70% yield by evaporation of solvent. Analysis: Calculated for ($NiC_{46}H_{64}N_2O_8$+$2H_2O$) (MW=868): Ni, 6.76; C, 63.67; H, 7.90; N, 3.23. Found: Ni, 6.72; C, 64.38; H, 7.78; N, 3.26. UV-Vis: (0.265 mM in $CH_2Cl_2$) [nm (ε×10$^3$ $M^{-1}$ $cm^{-1}$)]: 470 (br, 11.0), 407 (sh, 18.1), 386 (sh, 27.0), 370 (19.5), 297 (sh, 19.3), 266 (39.4). M.S.: [FAB$^+$ in 3-NBA] Calculated (M—$CH_3OH$) m/e=832, found 831. I.R.: [CsI, cm$^{-1}$] 2959 (vs), 2910 (m), 2868 (m), 1607 (s), 1591 (s), 1524 (s), 1516 (s), 1507 (s), 1465 (m), 1430 (m), 1414 (m), 1388 (m), 1359 (s), 1329 (w), 1279 (s), 1255 (m), 1239 (w), 1195 (s), 1178 (vs), 1131 (s), 1119 (s),1056 (w), 974 (w), 956 (w), 936 (w), 842 (w), 787 (w), 584.0 (w), 572.3 (w), 543 (w), 508.7 (w). Far-I.R.: [CsI, cm$^{-1}$] 386.9, 343.1. $^1$H NMR [In $CD_2Cl_2$-$d_2$, 300 MHz, ppm.] Aromatic protons δ=8.036 (s, 2H), 7.388 (d, 2H, J=2.4 Hz), 7.162 (d, 2H, J=2.4 Hz), 7.142 (s, 2H); Crown protons δ=4.230 (m, 2H), 3.900 (m, 2H), 3.717 (m, 2H), 3.660 (m, 2H), 3.620 (s, 2H); Tertiary butyl protons δ=1.444 (s, 18H), 1.317 (s, 18H); Water 1.56 (s).

EXAMPLE 4

Preparation of Potassium Nickel-4,5-di(3,5-ditertiarybutylsalicylideneimine)benzo-18-crown-6 chloride [(K—Ni—I)$^+$Cl$^-$]

An amount of potassium chloride (3.01 mmol, 0.22 g) was dissolved in methanol (50 mL) and added to nickel-4,5-di (3,5-ditertiarybutylsalicylideneimine)benzo-18-crown-6 (0.602 mmol, 0.5 g) dissolved in acetone (50 mL). The intense red color remains unchanged. The K$^+$ complex was precipitated from the dark red solution by addition of water, and recrystallized from acetone/methanol solution to give potassium nickel-4,5-di(3,5-ditertiarybutylsalicylideneimine)benzo-18-crown-6 chloride in 80% yield. Analysis: Calculated for $(KNiC_{46}H_{64}N_2O_8I+H_2O)$ (MW=1016): Ni, 5.78; C, 54.39; H, 6.55; N, 2.76. Found: Ni, 4.74; C, 54.43; H, 6.59; N, 2.73. UV-Vis: (0.480 mM in $CH_2Cl_2$) [nm ($\epsilon \times 10^3$ $M^{-1}$ $cm^{-1}$)]: 498 (br, 11.8), 406 (sh, 22.4), 387 (34.3), 371 (24.1), 351 (sh, 14.6), 299 (21.7), 266 (45.0), 236 (44.6). M.S.: [FAB$^+$ in 3-NBA] Calculated m/e (M—I$^-$—H$_2$O) =869, found 869. I.R.: [CsI, cm$^{31}$ $^1$] 2959 (vs), 2910 (m), 2868 (m), 1613 (vs), 1605 (vs), 1590 (vs), 1528 (vs), 1521 (vs), 1466 (s), 1458 (s), 1430 (s), 1388 (s), 1360 (s), 1328 (m), 1278 (vs), 1253 (s), 1241 (m), 1197 (vs), 1177 (vs), 1134 (s), 1116 (s), 1053 (s), 1032 (m), 973.7 (m), 959.8 (m), 939.5 (m), 918.5 (w), 907.3 (w), 857.5 (w), 840.9 (m), 818.9 (w), 787.5 (m), 750.1 (w), 638.1 (w), 616.1 (w), 584.0 (w), 571.4 (w), 541.6 (m), 515.1 (w), 507.7 (w), 476.1 (w), 457.3 (w), 442.0 (w), 421.7 (w), 415.9 (w). $^1$H NMR [In $CD_2Cl_2$, 300 MHz, ppm]. Aromatic protons $\delta$=8.036 (s, 2H), 7.388 (d, 2H, J=2.4 Hz), 7.162 (d, 2H, J=2.4 Hz), 7.142 (s, 2H); Crown protons $\delta$=4.230 (m, 2H), 3.900 (m, 2H), 3.717 (m, 2H), 3.660 (m, 2H), 3.620 (s, 2H); Tertiary butyl protons $\delta$=1.444 (s, 18H); 1.317 (s, 18H).

EXAMPLE 5

Potassium Nickel 4,5-di(3,5-di-tertiarybutylsalicylideneimine)benzo-18-crown-6 iodide [(K—Ni—I)$^+$I$^-$]

An amount of potassium iodide (3.01 mmol, 0.5 g) was dissolved in methanol (50 mL) and added to nickel 4,5-di(3,5-ditertiarybutylsalicylideneimine)benzo-18-crown-6 (0.602 mmol, 0.5 g) dissolved in acetone (50 mL). The intense red color remains unchanged. The K$^+$ complex of potassium nickel 4,5-di(3,5-ditertiarybutylsalicylideneimine)benzo-18crown-6 iodide was precipitated from the dark red solution by addition of water. Recrystallization from acetone/methanol solution gave potassium nickel 4,5-di(3,5-ditertiarybutylsalicylideneimine)benzo-18-crown-6 iodide in 80% yield. Analysis: Calculated for $(KNiC_{46}H_{64}N_2O_8I+H_2O)$(MW=1016): Ni, 5.78; C, 54.39; H, 6.55; N, 2.76. Found: Ni, 5.77; C, 54.43; H, 6.59; N, 2.73. UV-Vis: (0.480 mM in $CH_2Cl_2$) [nm ($\epsilon \times 10^3$ $M^{-1}$ $cm^{-1}$)]: 498 (br, 11.8), 406 (sh, 22.4), 387 (34.3), 371 (24.1), 351 (sh, 14.6), 299 (21.7), 266 (45.0), 236 (44.6). M.S.: [FAB$^+$ in 3-NBA] Calculated m/e (M—I$^-$—H$_2$O)=869, found 869. I.R.: [CsI, cm$^{-1}$] 2959 (vs), 2910 (m), 2868 (m), 1613 (vs), 1605 (vs), 1590 (vs), 1528 (vs), 1521 (vs), 1466 (s), 1458 (s), 1430 (s), 1388 (s), 1360 (s), 1328 (m), 1278 (vs), 1253 (s), 1241 (m), 1197 (vs), 1177 (vs), 1134 (s), 1116 (s), 1053 (s), 1032 (m), 973.7 (m), 959.8 (m), 939.5 (m), 918.5 (w), 907.3 (w), 857.5 (w), 840.9 (m), 818.9 (w), 787.5 (m), 750.1 (w), 638.1 (w), 616.1 (w), 584.0 (w), 571.4 (w), 541.6 (m), 515.1 (w), 507.7 (w), 476.1 (w), 457.3 (w), 442.0 (w), 421.7 (w), 415.9 (w). Far-I.R: [CsI, cm$^{-1}$] 396.5 (w), 386.6 (w). $^1$H NMR [In $CD_2Cl_2$-d$_2$, 300 MHz, ppm.] Aromatic protons $\delta$=8.036 (s, 2H), 7.388 (d, 2H, J=2.4 Hz), 7.162 (d, 2H, J=2.4 Hz), 7.142 (s, 2H); Crown protons $\delta$=4.230 (m, 2H), 3.900 (m, 2H), 3.717 (m, 2H), 3.660 (m, 2H), 3.620 (s, 2H); Tertiary butyl protons $\delta$=1.44 4(s, 18H), 1.317 (s, 18H).

EXAMPLE 6

Preparation of Cesium Nickel-4,5-di(3,5-ditertiarybutylsalicylideneimine)benzo-18-crown-6 iodide [(Cs—Ni—I)$^+$I$^-$]

An amount of cesium iodide (3.01 mmol) was dissolved in methanol (50 mL) and added to nickel-4,5-di(3,5-ditertiarybutylsalicylideneimine)benzo-18-crown-6 (0.602 mmol, 0.5 g) dissolved in acetone (50 mL). The Cs$^+$ complex was precipitated by addition of water, and recrystallized from acetone/methanol solution to give cesium nickel-4,5-di(3,5-ditertiarybutylsalicylideneimine)benzo-18-crown-6 iodide in 85% yield. Analysis: Calculated for $(CsNiC_{46}H_{64}N_2O_8I)$(MW=1092): Ni, 5.38; C, 50.62; H, 5.91; N, 2.57. Found: Ni, 5.08; C, 50.95; H, 5.88; N, 2.58. UV-Vis: (0.120 mM in $CH_2Cl_2$) [nm ($\epsilon \times 10^3$ $M^1$ $cm^{-1}$)]: 496 (br, 10.9), 463 (sh, 9.1), 406 (sh, 20.1), 387 (30.7), 372 (sh, 22.8), 296 (sh, 25.9), 266 (50.4). M.S.: [FAB$^+$ in 3-NBA] Calculated m/e [(M—I$^-$)$_2$]=1929, found for the dimer of nickel 4,5-di(3,5-ditertiarybutylsalicylideneimine)(cesium benzo-18-crown-6-iodide)=1928. I.R.: [CsI, cm$^{-1}$] 2959 (vs), 2910 (m), 2868 (m), 1614 (s), 1591 (s), 1527 (s), 1508 (s), 1465 (s), 1432 (s), 1389 (m), 1360 (s), 1328 (m), 1277 (s), 1254 (s), 1197 (s), 1177 (vs), 1118 (s), 1056 (m), 1030 (w), 956.4 (m), 918.3 (w), 905.2 (vw), 879.1 (vw), 857.8 (vw), 841.8 (w), 787.3 (w), 773.1 (vw), 583.2 (vw), 572.9 (vw), 541.9 (w), 508.3 (vw). Far-I.R: [CsI, cm$^{-1}$] 386.9 (vw). $^1$H NMR [In $CD_2Cl_2$-d$_2$, 300 MHz, ppm.] Aromatic protons $\delta$=8.741 (s, 2H), 8.513 (s, 2H), 7.642 (s, 4H), 7.426 (d, 4H, J =4.04 Hz), 7.329 (s, 2H), 6.903 (s, 2H); Crown protons $\delta$=4.412 (m, 2H), 4.305 (m, 2H), 3.854 (m, 4H), 3.627 (m, 2H), 3.666 (m, 2H), 3.556 (s, 4H), 3.456 (m, 4H); Tertiary butyl protons $\delta$=1.472 (s, 18H), 1.427 (s, 18H), 1.346 (s, 18H), 1.319 (s, 18H). [In DMSO-d$_6$, 300 MHz, ppm.] Aromatic protons $\delta$=8.618 (s, 2H), 7.678 (s, 2H), 7.383 (d, 2H, J =2.78Hz), 7.300 (d, 2H, J=2.78 Hz); Crown protons $\delta$=4.272 (m, 2H), 3.819 (m, 2H), 3.633 (m, 2H), 3.576 (m, 2H), 3.539 (s, 2H); Tertiary butyl protons $\delta$=1.385 (s, 18H), 1.282 (s, 18H).

EXAMPLE 7

Preparation of Cesium bis-Nickel-4,5-di(3,5-ditertiarybutylsalicylideneimine)benzo-18-crown-6 iodide [(Cs—Ni—I)$_2$+I$^-$]

An amount of cesium iodide (1.50 mmol) was dissolved in methanol (50 mL) and added to nickel-4,5-di(3,5-ditertiarybutylsalicylideneimine)benzo-18-crown-6 (0.602 mmol, 0.5 g) dissolved in acetone (50 mL). The Cs$^+$ complex was precipitated by addition of water, and recrystallized from acetone/2-propanol solution to give cesium bis-nickel-4,5-di(3,5-ditertiarybutylsalicylideneimine)benzo-18-crown-6 iodide in 85% yield. Analysis: Calculated for $(CsNi_2C_{92}H_{128}N_4O_{16}I)$(MW=1923): Ni, 6.10; C, 57.45; H, 6.71; N, 2.91. Found: Ni, 5.30; C, 58.08; H, 6.74; N, 2.91. UV-Vis: (0.138 mM in $CH_2C l_2$) [mn ($\epsilon \times 10^3$ $M^{-1}$ $cm^{-1}$)]: 496 (br, 8.10), 402 (sh, 30.3), 386 (41.3), 369 (38.5), 305 (sh, 30.6), 292 (sh, 36.1), 270 (50.6), 238 (63.4). M.S.: [FAB$^+$ in 3-NBA] Calculated m/e (M—I)=1796, found 1796. I.R.: [CsI, cm$^{-1}$] 2959 (vs), 2910 (m), 2868 (m), 1612 (s), 1591 (s), 1526 (s), 1509 (s), 1464 (m), 1432 (m), 1403 (m), 1389 (s), 1359 (m), 1328 (w), 1277 (s), 1254 (m), 1195 (s), 1176 (vs), 1118 (s), 1062 (m), 1028 (w), 958.9 (m), 918.0 (vw), 831.6 (vw), 787.3 (w), 731.3 (vw), 637.5 (vw), 615.3 (vw), 583.4 (vw), 542.3 (w), 509.2 (vw). Far-I.R: [CsI, cm$^{-1}$] none observed. $^1$H NMR [In $CD_2Cl_2$-d$_2$, 300 MHz, ppm.] Aromatic protons $\delta$=8.777 (s, 2H), 8.675 (s, 2H) 7.811 (s, 2H), 7.509 (s, 2H), 7.642 (s, 2H), 7.446 (d, 2H, J=2.34 Hz), 7.424 (d, 2H, J=2.34 Hz), 7.352 (s, 2H), 7.323 (s, 2H), 6.920 (s, 2H); Crown protons $\epsilon$=4.418 (m, 4H), 4.305 (m, 4H), 3.831 (m, 4H), 3.649 (m, 4H), 3.620 (m, 4H), 3.550 (m, ( 4H), 3.518 (m, 4H), 3.496 (m, 4H), 3.434 (m, 8H); Tertiary butyl protons $\epsilon$=1.478 (s, 18H), 1.432 (s, 18H), 1.352 (s, 18H), 1.325 (s, 18H).

EXAMPLE 8

Preparation of Nickel 4,5-di(3,5-ditertiarybutylsalicylideneimine)benzo-18-crown-6-n-hexylammonium Chloride [(Ni—I—HexNH$_3$)$^+$Cl$^-$]

An amount of hexylammonium chloride (0.120 mmol, 0.0165 g) was dissolved in methanol (10 mL) and added to nickel-4,5-di(3,5-ditertiarybutylsalicylideneimine)benzo-18crown-6 (0.120 mmol, 0.10 g) dissolved in acetone (50 mL). The intense red color remains unchanged. The complex was precipitated from the dark red solution by slow evaporation of acetone. Large blocks of crystals were obtained which readily lose solvents of crystallization, to give nickel 4,5-di(3,5-ditertiarybutylsalicylideneimine)benzo-18-crown-6-n-hexylammonium chloride in 40% yield. Analysis: Calculated for (NiC$_{52}$H$_{80}$N$_3$O$_8$Cl+Acetone)(MW=1026): Ni, 5.71; C, 64.29; H, 8.43; N, 4.09. Found: Ni, 5.70; C, 63.53; H, 8.46; N, 4.20. UV-Vis: (0.380 mM in CH$_2$Cl$_2$) [nm ($\epsilon \times 10^3$ M$^{-1}$ cm$^{-1}$)]: 498 (br, 12.1), 465 (sh, 9.75), 407 (sh, 22.3), 388 (34.9), 371 (sh, 23.9), 299 (21.3), 267 (45.4), 240 (sh, 33.4). I.R.: [CsI, cm$^{-1}$] 3195 (w), 2959 (vs), 2910 (m), 2868 (m), 1613 (s), 1607 (s), 1527 (s), 1514 (s), 1465 (m), 1431 (m), 1388 (m), 1359 (s), 1329 (w), 1278 (vs), 1255 (m), 1196 (s), 1178 (vs), 1133 (s), 1115 (s), 1056 (m), 972.9 (m), 959.4 (m), 918.5 (w), 906.0 (vw), 861.3 (vw), 842.0 (w), 787.5 (w), 749.6 (vw), 638.6 (vw), 617.4 (vw), 584.3 (vw), 542.7 (w), 508.1 (vw), 470.1 (vw), 440.6 (vw), 413.9 (vw). Far-I.R: [CsI, cm$^{-1}$] 385.8 (w). $^1$H NMR [In Acetone-d$_6$, 300 MHz, ppm.] Aromatic protons $\delta$=8.638 (s, 2H), 7.697 (d, 2H, J=2.4 Hz), 7.420 (d, 2H, J=2.4 Hz), 7.332 (s, 2H); Crown protons $\delta$=4.263 (m, 2H), 3.903 (m, 2H), 3.716 (m, 2H), 3.659 (m, 2H), 3.624 (s, 2H); Tertiary butyl protons $\delta$=1.487 (s, 18H), 1.303 (s, 18H); Hexylammonium protons that were found $\delta$=3.354, 3.126, 2.962, 1.783, 0.882 all broad. Acetone $\delta$=2.05.

EXAMPLE 9

Preparation of Chloro-Manganese (III)-4,5-di(3,5-ditertiarybutylsalicylideneimine)benzo-18crown-6 [Mn(III)—I—(H$_2$O)(EtOH)]$^+$Cl$^-$ An amount of manganese (II) chloride (0.646 mmol, 0.081 g) is dissolved in ethanol (50 mL) and added to a solution of 4,5-di(3,5-ditertiarybutylsalicylideneimine) benzo-18crown-6 (0.646 mmol, 0.5 g) in CH$_2$Cl$_2$ (50 mL). The resulting yellow brown solution was allowed to stir in air to oxidize overnight. Chloro-Manganese (III)-4,5-di(3,5-ditertiarybutylsalicylideneimine)benzo-18-crown-6 was isolated after evaporation of solvent in 65% yield. Analysis: Calculated for (MnC$_{46}$H$_{64}$N$_2$O$_8$Cl+CH$_3$CH$_2$OH+H$_2$O) (MW=927.5): Mn, 5.92; C, 62.15; H, 7.82; N, 3.02. Found: Mn, 5.87; C, 61.95; H, 7.79; N, 3.09. UV-Vis: (0.104 mM in CH$_2$C$_2$)[nm ($\epsilon \times 10^3$ M$^{-1}$ cm$^{-1}$)]: 483 (br, 12.2), 380(20.5), 364(sh, 19.7), 319(20.9), 263(30.4). M.S.: [FAB$^+$ in 3-NBA] Calculated m/e (M—CH$_3$CH$_2$OH—H$_2$O—Cl$^-$) $^-$828, found 827. I.R.: [CsI, cm$^{-1}$] 2959 (vs), 2910 (m), 2868 (m), 1605 (vs), 1585 (s), 1552 (s), 1531 (vs), 1513 (s), 1463 (s), 1427 (s), 1410 (m), 1389 (s), 1378 (s), 1361 (vs), 1326 (m), 1310 (s), 1273 (vs), 1250 (s), 1196 (s), 1179 (s), 1134 (s), 1116 (s), 1054 (m), 1029 (m), 966.7 (m), 932.5 (m), 918.7 (m), 841.7 (s), 820.2 (m), 780.2 (m), 751.8 (m), 639.8 (w), 612.6(w), 558.1 (m), 545.4 (m), 493.8 (w). Far-I.R.: [CsI, cm$^{-1}$] 393.0, 358.8. Magnetic moment, $\mu_{eff}^{corr}$: 300K, 4.41 B.M.; 4K, 4.38 B.M.

EXAMPLE 10

Preparation of Chloro-manganese (III)-4,5-di(3,5-ditertiarybutylsalicylideneimine)(potassium benzo-18-crown-6-iodide) [K—Mn—I]

An amount of potassium iodide (3.01 mmol, 0.5 g) was dissolved in methanol (50 mL) and added to chloro-manganese (III)-4,5-di(3,5-ditertiarybutylsalicylideneimine)benzo-18crown-6 (0.602 mmol) dissolved in acetone (50 mL). The K$^+$ complex was isolated by solvent evaporation to give chloro-manganese (III)-4,5-di(3,5-ditertiarybutylsalicylideneimine)(potassium benzo-18-crown-6-iodide) in 60% yield. Analysis: Calculated for (KMnC$_{46}$H$_{64}$N$_2$O$_8$ClI+4H$_2$O)(MW=1101.5): Mn, 4.98; C, 50.16; H, 6.59; N, 2.54. Found: Mn, 4.75; C, 50.19; H, 6.22; N, 3.10. UV-Vis: (0.352 mM in CH$_2$Cl$_2$) [nm ($\epsilon \times 10^3$ M$^{-1}$ cm$^{-1}$)]: 500(br, 8.0), 419(sh, 14.5), 384(sh, 21.6), 354(23.8), 326)(sh, 21.6), 259(29.1). M.S.: [FAB$^+$ in 3-NBA] Calculated m/e (M—4H$_2$O—Cl$^-$—I$^-$—H$^{3o}$)=866, found 866. I.R.: [CsI, cm$^{-1}$] 2959 (vs), 2910 (m), 2868 (m), 1607 (vs), 1585 (s), 1531 (vs), 1512 (s), 1463 (s), 1428 (m), 1411 (m), 1390 (s), 1378 (s), 1362 (s), 1308 (s), 1273 (vs), 1250 (s), 1196 (s), 1179(s), 1135 (s), 1117 (s), 1053 (m), 1030(w), 988.5 (w), 967.0(m), 931.4(w), 918.0(w), 897.4 (w), 841. 7(m), 820.1 (w), 779.6 (w), 752.6 (w), 639.8 (vw), 612.5 (vw), 559.5 (m), 546.0 (m), 500.3 (w), 493.3 (w), 455.1 (w). Far-I.R.: [CsI, cm$^{-1}$] 360.8 (w). Magnetic moment, $\mu_{eff}^{corr}$: 300K, 5.08 B.M.; 4K, 4.87 B.M.

EXAMPLE 11

Preparation of Bis[(iodo)-manganese (III)-4,5-di(3,5-ditertiarybutylsalicylideneimine)(cesium benzo-18-crown-6 chloride)] [Cs—Mn—(I)$_2$]

An amount of cesium iodide (3.00 mmol) was dissolved in methanol (50 mL) and added to chloro- manganese (III)-4,5-di(3,5-ditertiarybutylsalicylideneimine)benzo-18-crown-6 (0.602 mmol) dissolved in acetone (50 mL). The Cs$^+$ complex was precipitated by addition of water. The solid was redissolved in acetone/methanol solution, and cesium iodide (1.50 mmol) was added during recrystallization. Recrystallization gave bis[(iodo)-manganese (III)4,5-di(3,5-ditertiarybutylsalicylidene benzo-18-crown-6 chloride)] in 90% yield. Analysis: Calculated for (CsMn$_2$C$_{92}$H$_{128}$N$_4$O$_{16}$ClI$_2$+4H$_2$O)(MW=2150): Mn, 5.11; C, 51.39; H, 6.38; N, 2.61. Found: Mn, 4.48; C, 51.01; H, 6.15; N, 2.61. UV-Vis: (0.077 mM in CH$_2$Cl$_2$) [nm ($\epsilon \times 10^3$ M$^{-1}$ cm$^{-1}$)]: 491 (br, 25.6), 379 (55.1), 354 (56.3), 321 (55.3), 260 (77.0). M.S.: [FAB$^+$ in 3-NBA] Calculated m/e (M—4H$_2$O—I$^-$)=1951, found 1949. I.R.: [CsI, cm$^{-1}$] 2959 (vs), 2910 (m), 2868 (m), 1606 (vs), 1583 (s), 1531 (vs), 1463 (m), 1425 (m), 1411 (m), 1389(s), 1377(s), 1361 (s), 1311 (m), 1271 (vs), 1250(s), 1195 (s), 1180(s), 1114 (s), 1053 (w), 1032 (w), 960.2 (m), 919.8 (vw), 902.6 (vw), 841.6 (m), 780.2 (w), 750.9 (w), 640.7 (vw), 611.3 (vw), 558.0 (m), 545.4 (m), 493.8 (w), 451.9 (vw), 412.6 (vw). Far-I.R.: [CsI, cm$^{-1}$] 366.2 (vw), 355.6 (w). Magnetic moment, $\mu_{eff}^{corr}$: 300K, 6.80B.M.; 4K, 6.26B.M.

EXAMPLE 12

Preparation of Iodo-manganese (III)-4,5-di(3,5-ditertiarybutylsalicylideneimine)(cesium benzo-18-crown-6-iodide) [Cs—Mn—I]

An amount of cesium iodide (3.00 mmol) was dissolved in methanol (50 mL) and added to chloro- manganese (III)-4,5-di(3,5-ditertiarybutylsalicylideneimine)benzo-18-crown-6 (0.602 mmol) dissolved in acetone (50 mL). The Cs$^+$ complex was precipitated by addition of water. The solid was redissolved in acetone/methanol solution, and excess cesium iodide was added during recrystallization. Recrystallization gave iodo-manganese (III)-4,5-di(3,5-ditertiarybutylsalicylideneimine) (cesium benzo-18-crown-6 iodide) in 85% yield. Analysis: Calculated for (CsMnC$_{46}$H$_{64}$N$_2$O$_8$I$_2$+2CH$_3$OH)(MW=1278): Mn, 4.30; C, 45.08; H, 5.67; N, 2.19. Found: Mn, 4.49; C, 44.99; H, 5.47; N, 2.20. M.S.: [FAB$^+$ in 3-NBA] Calculated m/e (M—I$^-$—2CH$_3$OH)=1087, found 1087. I.R.:[KBr, cm$^{-1}$] 2959 (vs), 2910 (m), 2868 (m), 1605 (s), 1585 (s), 1550 (m), 1531 (vs), 1511 (s), 1462 (m), 1427 (m), 1411(w), 1388 (s), 1378 (s), 1361 (s), 1309 (m), 1271 (vs), 1250 (s), 1196 (s), 1178 (s), 1113(s), 1052 (m), 961.6 (m), 919.2 (vw), 904.1 (vw), 841.9 (m), 819.3 (w), 779.0 (w), 751.9 (w), 612.4 (vw), 580.2 (w), 558.6 (m), 546.1 (m), 497.4 (w). Far-I.R.: [CsI, cm$^{-1}$] 396.7 (vw), 374.2 (vw), 364.3 (vw), 351.7 (w). Magnetic moment, $\mu_{eff}^{corr}$: 300K, 5.38B.M.; 4K, 4.95B.M.

EXAMPLE 13

Preparation of Copper 4,5-di(3,5-ditertiarybutylsalicylideneimine)benzo-18-crown-6 [Cu—I]

An amount of copper acetate (0.646 mmol, 0.13 g) was dissolved in methanol (50 mL) and added to a solution of 4,5-di(3,5-ditertiarybutylsalicylideneimine)benzo-18-crown-6 (0.646 mmol, 0.5 g) in methylene chloride (50 mL). A brown solution was obtained, giving a brown powder upon evaporation. Evaporation of methylene chloride/methanol solution of the copper complex gave fibrous crystals of copper 4,5-di(3,5-ditertiarybutylsalicylideneimine) benzo-18crown-6 in 80% yield. Analysis: Calculated for (CuC$_{46}$H$_{64}$N$_2$O$_8$+2CH$_3$OH) (MW=901): Cu, 7.06; C, 64.01; H, 8.06; N, 3.11. Found: Cu, 6.84; C, 64.15; H, 7.95; N, 3.19. UV-Vis: (0.113 mM in CH$_2$Cl$_2$) [nm ($\epsilon \times 10^3$ M$^{-1}$ cm$^{-1}$)]: 487 (sh, 13.3), 444 (24.3), 419 (25.4), 398 (sh, 19.5), 371 (20.0), 350 (18.0), 319 (24.7), 306 (23.4), 289 (23.4), 249 (32.4). M.S.: [FAB$^+$ in 3-NBA] Calculated m/e (M-2CH$_3$OH)=837, found 835. I.R.: [CsI, cm$^{-1}$] 2959 (vs), 2910 (m), 2868 (m), 1608 (vs), 1589 (s), 1544 (m), 1525 (s), 1504 (s), 1464 (m), 1431 (m), 1411 (m), 1358 (m), 1329 (w), 1271 (s), 1233 (w), 1217 (w), 1190 (m), 1173 (vs), 1133 (s), 1058 (m), 1027 (w), 967.1 (w), 950.6 (w), 932.2 (w), 916.0 (w), 866.9 (w), 838.4 (w), 815.0 (w), 790.5 (m), 746.7 (w), 637.1 (w), 581.2 (w), 533.4 (w), 505.6 (w), 496.3 (w). Far-I.R.: [CsI, cm$^{-1}$] 390.7, 353.8, 342.2, 329.3. Magnetic moment, $\mu_{eff}^{corr}$: 300K, 1.85 B.M.; 4K, 1.72 B.M.

EXAMPLE 14

Preparation of Copper 4,5-di(3,5-ditertiarybutylsalicylideneimine)potassium benzo-18-crown-6 iodide [K—Cu—I]

An amount of potassium iodide (3.01 mmol, 0.5 g) was dissolved in methanol (50 mL) and added to copper 4,5-di(3,5-di-tertiarybutylsalicylideneimine)benzo-1-crown-6 (0.602 mmol) dissolved in acetone (50 mL). Evaporation of an acetone/methanol/water mixed solution of the copper complex gave copper 4,5-di(3,5-ditertiarybutylsalicylideneimine) potassium benzo-18-crown-6 iodide in 80% yield. Analysis: Calculated for (KCuC$_{48}$H$_{72}$N$_2$O$_{10}$I+4H$_2$O)(MW=1075): Cu, 5.91; C, 51.41; H, 6.75; N, 2.61. Found: Cu, 5.86; C, 51.94; H, 6.48; N, 2.53. UV-Vis: (0.420 mM in CH$_2$C l$_2$) [nm ($\epsilon \times 10^3$ M$^{-1}$ cm$^{-1}$)]: 484 (sh, 13.2), 448 (21.9), 419 (21.7), 399 (sh, 16.9), 370 (18.3), 348 (17.7), 318 (23.2), 305 (21.2), 289 (21.5), 236 (40.5). M.S.: [FAB$^{30}$ in 3-NBA] Calculated m/e (M—4H$_2$O—I$^-$) =876, found 874. I.R.: [CsI, cm$^{-1}$] 2959 (vs), 2910 (m), 2868 (m), 1607 (vs), 1589 (s), 1525 (vs), 1509 (s), 1463 (s), 1430 (s), 1411 (m), 1385 (s), 1365 (s), 1358 (m), 1328 (w), 1269 (vs), 1252 (s), 1237 (m), 1194 (s), 1173 (vs), 1134 (s), 1117 (s), 1064 (w), 1053 (m), 1031 (w), 963.6 (s), 916.1 (w), 907.2 (w), 878.8 (w), 859.0 (w), 836.7 (m), 815.4 (w), 791.1 (m), 747.1 (w), 694.8 (w), 665.0 (w), 637.6 (w), 610.6 (w), 582.1 (w), 533.5 (m), 504.5 (w), 496.2 (w). Far-I.R.: [CsI, cm$^{-1}$] 342.6 (w). Magnetic moment, $\mu_{eff}^{corr}$: 300K, 1.86 B.M.; 4K, 1.82 B.M.

EXAMPLE 15

Preparation of Cobalt 4,5-di(3,5-ditertiarybutylsalicylideneimine)benzo-18-crown-6

An amount of cobalt acetate (0.646 mmol, 0.16 g) was dissolved in methanol (50 mL) and added to a solution of 4,5-di(3,5-tertiarybutylsalicylideneimine)benzo-18-crown-6 (0.646 mmol, 0.5 g) in methylene chloride (50 mL) under an inert atmosphere. Evaporation of a methylene chloride/methanol solution of the cobalt complex under an inert N$_2$ atmosphere gave cobalt 4,5-di(3,5-ditertiarybutylsalicylideneimine)benzo-18-crown-6 crystals, which were isolated by filtration. The product was obtained in 60% yield and stored under nitrogen. Analysis: Calculated for (CoC$_{46}$H$_{64}$N$_2$O$_8$)(MW=832): Co, 7.08; C, 66.41; H, 7.75; N, 3.37. Found: Co, 6.78; C, 66.78; H, 7.63; N, 3.40. UV-Vis: (0.32 mM in CH$_2$Cl$_2$)[ nm ($\epsilon \times 10^{-3}$ M$^{-1}$ cm$^{-1}$)]: 516 (sh, 2.67), 465 (sh, 7.76), 406 (19.4), 390 (sh, 17.4), 361 (18.1), 313 (18.1), 303 (19.0), 247 (sh, 31.8). M.S.: [FAB$^+$ in 3-NBA] Calculated m/e=832, found 832. I.R.: [CsI, cm$^{-1}$] 2959 (vs), 2910 (m), 2868 (m), 1614 (s), 1581 (s), 1521 (m), 1507 (vs), 1466 (s), 1427 (s), 1409 (m), 1390 (s), 1360 (s), 1325 (m), 1277 (vs), 1252 (s), 1232 (m), 1198 (s) 1180 (s), 1122 (s), 1058 (m), 1028 (w), 973.9 (m), 959.7 (m), 929.6 (w), 917.3 (m), 905.3 (w), 859.6 (w), 842.2 (m), 816.1 (w), 787.9 (m), 617.6 (w), 585.2 (w), 545.0 (m), 509.2 (w), 413.2 (w). Far-I.R.: [CsI, cm$^{-1}$] 396 (w), 381 (w). Magnetic moment, $\mu_{eff}^{corr}$: 300K, 2.03 B.M.; 4K, 2.05 B.M.

EXAMPLE 16

Preparation of Cobalt 4,5-di(3,5-ditertiarybutylsalicylideneimine) potassium benzo-18crown-6-iodide An amount of potassium iodide (3.01 mmol, 0.5 g) was dissolved in a minimal amount of water before dilution in methanol (50 mL), and added to cobalt 4,5-di(3,5-ditertiarybutylsalicylideneimine)benzo-18-6 (0.602 mmol, 0.5 g) dissolved in acetone (50 mL) under an inert atmosphere. Crystals of cobalt 4,5-di(3,5-ditertiarybutylsalicylideneimine) potassium benzo-18-crown-6 iodide were obtained by evaporating methylene chloride/methanol/water solution of the cobalt complex, under an inert N$_2$ atmosphere, followed by filtration. The product was obtained in 70% yield, and stored under nitrogen. Analysis: Calculated for (KCoC$_{46}$H$_{64}$N$_2$O$_8$I+2H$_2$O) (MW=1034): Co, 5.70; C, 5.43; H, 6.63; N, 2.71. Found: Co, 5.52; C, 53.47; H, 6.52; N, 2.77. UV-Vis: (0.213 mM in CH$_2$Cl$_2$) [nm ($\epsilon \times 10^{-3}$ M cm$^{-1}$)]: 594 (sh, 2.5), 541 (sh, 4.8), 463 (sh, 13.9), 431 (sh, 20.8), 407 (26.4), 362 (20.3), 343 (sh, 16.3), 314 (21.9), 303 (20.7), 234 (44.8). M.S: [FAB$^+$ in 3-NBA] Calculated m/e (M-2H$_2$O—I$^-$)=871, found 870. I.R.: [CsI, cm$^{-1}$] 2959 (vs), 2910 (m), 2868 (m), 1613 (m), 1603 (m), 1580 (s), 1544 (w), 1523 (s), 1462 (m), 1425 (m), 1388 (m), 1359 (s), 1324 (w), 1275 (vs), 1251 (s), 1196 (s), 1180 (s), 1115 (s), 1109 (s), 1068 (s), 1053 (m), 970.8 (m), 959.6 (m), 917.5 (w), 906.3 (w), 859.3 (w), 840.9 (w), 788.0 (m), 748.6 (w), 639.3 (w), 616.3 (w), 583.4 (w), 543.1 (w), 506.5 (w). Far-I.R.: [CsI, cm$^{-1}$] 382.7 (w). Magnetic moment, $\mu_{eff}^{corr}$: 300K, 2.12 B.M.; 4K, 1.86 B.M.

EXAMPLE 17

Preparation of Methoxy-iron (III) 4,5-di(3,5-ditertiarybutylsalicylideneimine)benzo-18-crown-6

In an inert atmosphere, an amount of anhydrous iron (III) chloride (0.646 mmol, 0.10 g) was dissolved in methanol (20 mL) and added dropwise through a coarse fritted funnel to a stirred methylene chloride solution of 4,5-di(3,5-ditertiarybutylsalicylideneimine)benzo-18crown-6 (0.646 mmol, 0.5 g), resulting in a yellow brown color. The resulting mixture was evaporated to dryness, redissolved in methylene chloride (50 mL), and filtered to remove the salt byproducts. Methanol (30 mL) was added to the filtrate, and the final solution was allowed to stand and evaporate. As the methylene chloride evaporated, dark brown crystals formed. The crystals were collected by filtration, and dried under vacuum to give methoxy-iron (III) 4,5-di(3,5-ditertiarybutylsalicylideneimine) benzo-18-crown-6 in 90% yield. Analysis: Calculated for ($FeC_{47}H_{67}N_2O_9$)(MW=860): Fe, 6.49; C, 65.65; H, 7.85; N, 3.26. Found: Fe, 6.10; C, 65.80; H, 7.63; N, 3.54. UV-Vis: (0.366 mM in MeOH) [nm ($\epsilon \times 10^3$ $M^{-1}$ $cm^{-1}$)]: 476 (sh, 8.7), 448 (sh, 11.2), 384 (sh, 18.6), 352 (sh, 21.5), 309 (28.0), 252 (sh, 20.4). M.S.: [$FAB^+$ in 3-NBA] Calculated m/e (M—$CH_3OH$)=828 found=828. I.R.: [CsI, $cm^{-1}$] 2959 (vs), 2910 (m), 2868 (m), 1608 (vs), 1584 (s), 1546 (m), 1528 (vs), 1504 (s), 1462 (s), 1429 (s), 1409 (m), 1387 (s), 1358 (s), 1319 (m), 1270 (vs), 1233 (m), 1202 (s), 1173 (vs), 1032 (s), 1121 (s), 1054 (m), 1027 (m), 991.7 (w), 950.5 (m), 933.6 (w), 916.4 (w), 869.5 (m), 839.4 (m), 815.6 (w), 786.6 (m), 746.7 (w), 537.3 (m), 490.4 (w), 479.6 (w), 452.9 (w). Far-I.R.: [CsI, $cm^{-1}$] 388.3 (w), 337.6 (w), 316.8 (w). Magnetic moment, $\mu_{eff}^{corr}$: 300K, 4.61 B.M.; 4K, 4.31 B.M.

EXAMPLE 18

Preparation of Methoxy-iron (III) 4,5-di(3,5-ditertiarybutylsalicylideneimine) potassium benzo-18-crown-6 chloride An amount of potassium iodide (3.01 mmol, 0.5 g) was dissolved in methanol (50 mL) and added to methoxy-iron (III) 4,5-di(3,5-ditertiarybutylsalicylideneimine)benzo-18-crown-6 (0.602 mmol) dissolved in acetone (50 mL). The complex was precipitated by addition of water. Crystals can be obtained by slow evaporation of an acetone/methanol solution of the methoxy-iron complex, with addition of potassium chloride (1 eq to 5 eq), to give methoxy-iron (III) 4,5-di(3,5-ditertiarybutylsalicylideneimine) potassium benzo-18-crown-6 chloride in 90% yield. Analysis: Calculated for ($KFeC_{47}H_{67}N_2O_9Cl$)(MW=934.5): Fe, 5.98; C, 60.41; H, 7.23; N, 3.00. Found: Fe, 5.40; C, 59.98; H, 7.44; N, 3.26. UV-Vis: (0.240 mM in $CH_2Cl_2$) [nm ($\epsilon \times 10^3$ $M^{-1}$ $cm^{-1}$)]: 453(sh, 10.7), 358(37.2), 296(49.5). M.S.: [$FAB^+$ in 3-NBA] Calculated m/e (M—$CH_3O^-$—$Cl^-$—$H^+$)=867, found=867. I.R.: [CsI, $cm^{-1}$] 2959 (vs), 2910 (m), 2868 (m), 1604 (s), 1581 (s), 1551 (w), 1530 (s), 1506 (s), 1461 (m), 1424 (m), 1411 (w), 1388 (m), 1377 (m), 1360 (s), 1312 (w), 1264 (vs), 1250 (s), 1202 (s), 1191 (s), 1176 (s), 1115 (vs), 1064 (m), 1050 (m), 1029 (m), 957.0 (m), 917.1 (w), 903.3 (w), 880.1 (w), 841.8 (m), 817.2 (w), 781.8 (w), 749.4 (w), 640.7 (w), 606.9 (w), 578.4 (w), 543.1 (m), 489.7 (w), 481.4 (w), 459.9 (w). Far-I.R.: [CsI, $cm^{-1}$] 340.5 (w). Magnetic moment, $\mu_{eff}^{corr}$: 300K, 5.35 B.M. 4K, 4.77 B.M.

EXAMPLE 19

Preparation of ($\mu^2$-oxo)-bis[(iron(III)-4,5-di(3,5-ditertiarybutylsalicylideneimine)(benzo-18crown-6)]

A quantity of methoxy-iron (III) 4,5-di(3,5-ditertiarybutylsalicylideneimine)benzo-18crown-6 (0.5 mM, 0.43 g) was dissolved in acetone (50 mL). To this was added (0.5 mM, 0.021 g) LiOH dissolved in water (30 mL). The mixture was stirred and acetone was evaporated under a stream of nitrogen. A solid precipitate forms, which was collected by filtration, and washed with deionized water (2×20 mL). The compound was dried under vacuum to give ($\mu^2$-oxo)-bis[(iron(III)-4,5-di(3,5-ditertiarybutylsalicylideneimine)(benzo-18crown-6)] in 90% yield. Analysis: Calculated for ($Fe_2C_{92}H_{128}N_4O_{17}$+$2H_2O$)(MW=1710): Fe, 6.53; C, 64.63; H, 7.78; N, 3.28. Found: Fe, 5.78; C, 63.53; H, 7.84; N, 3.24. UV-Vis: (0.194 mM in $CH_2Cl_2$) [nm ($\epsilon \times 10^3$ $M^{-1}$ $cm^{-1}$)]: 441 (sh, 24.3), 392 (sh, 34.6), 351 (sh, 50.9), 306 (61.5), 288 (sh, 54.8), 235 (sh, 53.6). M.S.: [$FAB^+$ in 3-NBA] Calculated m/e (M-$2H_2O$)= 1674, found 1673. I.R.: [CsI, $cm^{-1}$] 2959 (vs), 2910 (m), 2868 (m), 1608, 1584, 1546, 1528, 1504, 1462, 1429, 1409, 1387, 1358, 1319, 1270, 1234, 1217, 1202, 1173, 1132, 1121, 1054, 1027, 991.7, 950.5, 933.6, 916.4, 869.5, 839.4, 815.6, 786.6, 746.7, 537.3, 490.4, 479.6, 452.9. Far-I.R.: [CsI, $cm^{-1}$] 388.3 (w), 337.6 (w), 316.8 (w). Magnetic moment, $\mu_{eff}^{corr}$: 300K, 3.58 B.M. ; 4K, 1.91 B.M.

EXAMPLE 20

Preparation of ($\mu^2$-oxo)-bis[(iron(III)-4,5-di(3,5-ditertiarybutylsalicylideneimine)(potassium benzo-18-crown-6) iodide)]

Methoxy-iron (III) 4,5-di(3,5-ditertiarybutylsalicylideneimine)benzo-18-crown-6 (0.5 mM, 0.43 g) was dissolved in acetone (50 mL). To this solution was added LiOH (0.5 mM, 0.021 g) dissolved in water (30 mL). The reaction mixture was stirred and acetone was evaporated under a stream of nitrogen. A solid precipitate forms, which was collected by filtration, and washed with deionized water (2×20 mL). The solid recrystallized from acetone/ethanol with addition of potassium iodide (1 eq to 5 eq). Recrystallization from the solvent gave ($\mu^2$-oxo)-bis[(iron(III)-4,5-di(3,5-ditertiarybutylsalicylideneimine)(potassium benzo-18-crown-6) iodide)] in 90% yield. Analysis: Calculated for ($K_2Fe_2C_{92}H_{128}N_4O_{17}I_2$) (MW=2006): Fe, 5.57; C, 55.10; H, 6.43; N, 2.79. Found: Fe, 4.10; C, 54.83; H, 6.58; N, 2.79. UV-Vis: (0.187 mM in $CH_2Cl_2$) [nm ($\epsilon \times 10^3$ $M^{-1}$ $cm^{-1}$)]: 502 (sh, 13.7), 448 (24.2), 350 (sh, 41.2), 309 (60.9). M.S.: [$FAB^+$ in 3-NBA] Calculated m/e (M—$H^+$)=2005, found= 2001. I.R.: [CsI, $cm^{-1}$] 2959 (vs), 2910 (m), 2868 (m), 1609 (vs), 1585 (s), 1546 (m), 1529 (vs), 1505 (s), 1463 (s), 1430 (s), 1410 (m), 1387 (s), 1359 (s), 1320 (m), 1271 (vs), 1233 (m), 1203 (s), 1174 (vs), 1133 (s), 1122 (s), 1055 (m), 1028 (w), 991.9 (vw), 951.3 (w), 933.9 (w), 916.6 (w), 907.4 (vw), 870.4 (m), 840.0 (m), 816.1 (w), 787.3 (m), 747.1 (w), 583.2 (vw), 537.7 (m), 490.8 (w), 480.3 (w), 455.8 (w). Far-I.R.: [CsI, $cm^{-1}$] 388.3 (w), 338.5 (w), 318.6 (w). Magnetic moment, $\mu_{eff}^{corr}$: 300K, 3.18 B.M. ; 4K, 0.41 B.M.

EXAMPLE 21

Preparation of ($\mu$2-oxo)-bis[(iron(III)-4,5-di(3,5-ditertiarybutylsalicylideneimine)(cesium benzo-18-crown-6) iodide)]

Methoxy-iron (III) 4,5-di(3,5-ditertiarybutylsalicylideneimine)benzo-18-crown-6 (0.5 mM, 0.43 g) was dissolved in acetone (50 mL). To this solution was added LiOH (0.5 mM, 0.021 g) dissolved in water (30 mL). The reaction mixture was stirred and acetone was evaporated under a stream of nitrogen. A solid precipitate forms, which was collected by filtration, and washed with deionized water (2×20 mL). The solid was recrystallized from aceotne/water, and cesium iodide (1 eq to 5 eq) was added during recrystallization. After recrystallization, ($\mu^2$-oxo)-bis[(iron(III)-4,5-di(3,5-ditertiarybutylsalicylideneimine)(cesium benzo-18-crown-6) iodide)] crystals were collected in 90% yield. Analysis: Calculated for $(Cs_2Fe_2C_{92}H_{128}N_4O_{17}I_2+4H_2O)$(MW= 2265): Fe, 4.93; C, 48.78; H, 6.05; N, 2.47. Found: Fe, 4.57; C, 48.58; H, 5.88; N, 2.46. UV-Vis: (0.235 mM in $CH_2Cl_2$) [nm ($\epsilon \times 10^3$ $M^{-1}$ $cm^{-1}$)]: 441 (sh, 20.1), 390 (sh, 35.5), 350 (51.2), 304 (54.0), 286 (sh, 50.9), 235 (sh, 67.1). M.S.: [$FAB^+$ in 3-NBA] Calculated m/e (M—CsI—I⁻—4$H_2O$)= 1806, found=1809. I.R.: [CsI, $cm^{-1}$] 2959 (vs), 2910 (m), 2868 (m), 1608 (vs), 1585 (s), 1531 (s), 1507 (s), 1463 (m), 1442 (m), 1430 (m), 1411 (w), 1388 (m), 1379 (m), 1361 (s), 1313 (w), 1269 (vs), 1253 (s), 1202 (s), 1174 (vs), 1119 (vs), 1057 (m), 1028 (w), 956.0 (m), 917.1 (vw), 904.5 (vw), 873.7 (w), 841.5 (m), 817.6 (vw), 784.8 (w), 749.3 (vw), 687.5 (vw), 642.4 (vw), 606.8 (vw), 580.7 (vw), 541.5 (w), 489.8 (vw), 481.4 (vw). Far-I.R.: [CsI, $cm^{-1}$] 376.3 (vw), 369.3 (vw), 360.8 (vw). Magnetic moment, $\mu_{eff}^{corr}$: 300K, 3.20 B.M. ; 4K, 1.62 B.M.

EXAMPLE 22

Preparation of N,N'-4,5-dimethoxybenzenebis(3,5-di-tertiarybutylsalicylideneimine)

An amount of concentrated nitric acid (100 mL) was added to deionized water (100 mL) in an ice bath, followed by dropwise addition of veratrole (0.314 mol, 40 mL). Once addition was complete the solution was heated to 60° C., and stirred until no more nitrogen dioxide evolves. This solution was then poured over ice (1 L), and placed into a large Buchner funnel. After vacuum filtration, a yellow mushy solid was isolated. The solid was washed with several portions of deionized water (2×100 mL), and several portion of saturated sodium bicarbonate solution until no gas evolves. The filtrate was washed again with deionized water c (2×100 mL), and the product was air-dried. The yellow solid was dissolved in boiling ethanol (1 L), which crystallizes upon cooling. The crystals were recovered by filtration to give 4,5-dinitroveratrole in 90% yield.

An amount of 4,5-dinitroveratrole, (43 mmol, 10 g), palladium (1 g) on activated carbon, and ethanol (200 mL) are combined with stirring. After attaching a condenser, hydrazine monohydrate (23 mL) was added slowly from the top. The solution turns red and froths immediately. A nitrogen inlet was attached to the condenser immediately after addition of the monohydrate. The reaction mixture was heated and stirred after frothing stops. After about fifteen minutes a vigorous evolution of gas occurs and the solution color changes from red to yellow, and finally to a colorless solution. The reaction was stirred for one hour at reflux and then filtered through Celite under Schlenk conditions. The solvent was removed from the product using a cold trap, to give off-white 4,5-diamineveratrole solid. The solid was washed under an inert atmosphere with ether (50 mL), followed by isopropanol (30 mL) to remove color, and finally with ether again (50 mL). The solid was air-dried after washing, and stored under nitrogen. $^1H$ NMR in DMSO-$d_6$ with TMS as standard. [ppm, M, #H]; Methoxy δ=3.57 (s, 6H); Amine δ=4.07 (s, 4H); Aromatic δ=6.26 (s, 2H). $^{13}C$ NMR in DMSO-$d_6$ with TMS as standard. Aromatic carbons: Calculated δ=102.1, 126.6, 135.2. Found δ=103.1, 128.6, 140.1. Literature δ=56.51, 103.54, 127.53, 142.81.

An amount of 4,5-diamineveratrole (10 mmol, 1.70 g) was added to methanol (70 mL) with stirring under inert atmosphere, giving a colorless solution. To this solution was added 3,5-di-tertarybutylsalicylaldehyde (20 mmol, 4.77 g) as a solid, with stirring of the reaction mixture to dissolve the aldehyde. The resulting bright yellow solution was refluxed for 18 hours. Monitoring by TLC showed minimal change after 18 hours. The solvent was removed using a cold trap, and the dark yellow tar was redissolved in a minimal amount of hexanes/ether (5:1), or in acetonitrile. The solution was filtered to remove the salts. The filtered solution was then placed in a freezer to induce precipitation of yellow crystalline product. The crystalline product was collected by filtration in air, and dried overnight under vacuum, to give N,N'-4,5-dimethoxybenzenebis(3,5-ditertiarybutylsalicylideneimine) in 70% yield. Analysis: Calculated for $(C_{38}H_{54}N_2O_4)$(MW=600): C, 75.96; H, 8.72; N, 4.66. Found: C, 76.01; H, 8.67; N, 4.65. M.S.: (EI 70EV) Calculated 600, found 600. UV-Vis.: (0.160 mM in MeOH) [nm, $\epsilon=10^3$ $M^{-1}$ $cm^{-1}$] 400 (sh, 19.1), 354 (br, 28.0), 276 (35.9), 237 (sh, 39.3). I.R.: [CsI, $cm^{-1}$]; 2959 (vs), 2910 (s), 2868 (m), 1615 (vs), 1576 (s), 1511 (vs), 1465 (s), 1439 (s), 1394 (m), 1362 (m), 1326 (w), 1268 (s), 1251 (s), 1222 (s), 1208 (s), 1193 (s), 1172 (vs), 1133 (w), 1116 (w), 1037 (w), 1027 (w), 1007 (m), 984.0 (w), 921.2 (w), 904.5 (m), 878.7 (w), 849.7 (m), 831.8 (w), 804.9 (w), 773.8 (w), 731.3 (w), 686.1 (w), 644.7 (w), 533.1 (w). NMR: ($CD_2Cl_2$)[ppm, M, #H] $^1H$ NMR: Aromatic protons δ=8.71 (s, 2H), 7.44 (d, 2H), 7.28 (d, 2H), 6.87 (s, 2H); Tertiary butyl protons δ=1.43 (s, 18H), 1.33 (s, 18H); Methoxy protons δ=3.94 (s, 6H). $^{13}C$ NMR[ppm]: 101, 119, 127, 129, 136.8, 137.4, 141, 158, 160, 164. M.p.=186°–197° C.

EXAMPLE 23

Preparation of N,N'-4,5-dimethoxybenzenebis(3,5-ditertiarybutylsalicylideneimine)Nickel(II)

N,N'-4,5-dimethoxybenzenebis(3,5-di-tertiarybutylsalicylideneimine) ligand (5 mmol, 3.00 g) was added to methanol (100 mL), and the mixture was heated to boiling with stirring until all of the ligand was dissolved. Additional methanol was added at boiling as needed. Nickel acetate tetrahydrate (5 mmol, 1.25 g) dissolved in methanol (40 mL) was added to the boiling solution. A bright red or orange powder precipitates immediately. Stirring was continued as the reaction mixture was cooled to room temperature. The resulting orange red powder was collected by filtration and washed with ethanol (10 mL), and diethylether (40 mL). The product was dried under vacuum overnight to give N,N'-4,5-dimethoxybenzenebis (3,5-ditertiarytbutylsalicylideneimine)nickel(II) in >90% yield. Analysis: Calculated for $(NiC_{38}H_{52}N_2O_4)$(MW=658): Ni, 8.93; C, 69.41; H, 7.66; N, 4.26. Found: Ni, 8.04; C, 69.65; H, 7.57; N, 4.17. UV-Vis.: [nm, $\epsilon \times 10^3$ $M^{-1}$ $cm^{-1}$]: 496 (br, 14.6), 466 (sh, 12.1), 404 (sh, 27.0), 386 (42.1), 371 (sh, 29.1), 298 (25.2), 266 (55.5). I.R.: [CsI, $cm^{-1}$] 2959 (vs), 2910 (s), 2868 (m), 1614 (vs), 1590 (s), 1544 (m), 1519 (vs), 1502 (s), 1465 (m), 1453 (m), 1444 (m), 1429, 1410 (m), 1393 (m), 1359 (s), 1331 (w), 1285 (vs), 1257 (w), 1236 (w), 1223 (m), 1205 (m), 1192(s), 1175 (vs), 1131 (m), 1116 (w), 1045 (w), 1035 (w), 1027(w), 1014 (w), 932.2 (w), 915.4 (w), 863.2 (w), 843.2 (w), 819.2 (m), 785.4 (m), 564.3 (w), 537.2 (w), 510.6 (w), 492.1 (w). Far-I.R.: [CsI, $cm^{-1}$] 383.4. NMR: ($CD_2Cl_2$)[ppm, M, #H] $^1H$-NMR: Aromatic protons: 7.99 (s, 2H), 7.39 (d, 2H), 7.26 (d, 2H), 7.11 (d, 2H). Methoxy protons: 4.00 (s, 6H). Tertiary butyl protons: 1.47 (s, 18H), 1.32 (s, 18H). $^{13}C$ NMR[ppm]: 97.7, 120, 127, 131, 137, 138, 141, 150, 154, 164.

EXAMPLE 24

Preparation of N,N'-4,5-dimethoxybenzenebis(3,5-ditertiarybutylsalicylideneimine) Copper(II) [Ni ($^t$Bu$_4$salphen)-veratrol]

N,N'-4,5-dimethoxybenzenebis(3,5-di-tertiarybutylsalicylideneimine) ligand (5 mmol, 3.00 g) was added to methanol (100 mL), and the mixture was heated to boiling with stirring until all of the ligand was dissolved. Additional methanol was added at boiling as needed. Copper acetate hydrate (5 mmol, 1.00 g) dissolved in methanol (40 mL) was added to the boiling solution. A brown powder precipitates from solution. Stirring was continued as the reaction mixture was cooled to room temperature. The resulting brown powder was collected by filtration and washed with ethanol (10 mL), and diethylether (40 mL). The product was dried under vacuum overnight to give N,N'-4,5-dimethoxybenzenebis(3,5-di-tertiarybutylsalicylideneimine)copper(II) in 85% yield. Analysis: Calculated for $(CuC_{38}H_{52}N_2O_4)$(MW=662): Cu, 9.59; C, 68.91; H, 7.61; N, 4.23. Found: Cu, 10.2; C, 69.08; H, 7.66; N, 4.32. UV-Vis.: (0.266 mM in $CH_2Cl_2$) [nm, $\epsilon \times 10^3$ $M^{-1}$ $cm^{-1}$]: 445 (25.0), 418 (26.1), 398 (sh, 20.1), 371 (21.8), 350 (18.7), 318 (25.6), 306 (24.0), 288 (25.4), 249 (34.9). I.R.: [CsI, $cm^{-1}$]: 2960 (s), 2910 (m), 2868 (w), 1608 (vs), 1589 (s), 1545 (w), 1523 (vs), 1504 (s), 1464 (m), 1454 (m), 1443 (m), 1431 (m), 1409 (w), 1387 (m), 1359 (m), 1331 (w), 1277 (vs), 1256 (w), 1222 (m), 1191 (m), 1171 (vs), 1133 (m), 1116 (w), 1042 (w), 1027 (w), 1013 (w), 948.7 (w), 930.9 (w), 909.5 (w), 865.7 (w), 838.7 (w), 824.6 (w), 789.9 (m), 534.4 (m), 507.2 (w), 491.1(w). Far-I.R.: [CsI, $cm^{-1}$] 337.2. Magnetic moment, $\mu_{eff}^{corr}$: 300K, 2.25; 4K, 1.05.

EXAMPLE 25

Preparation of N,N'-4,5-dimethoxybenzenebis(3,5-ditertiarybutylsalicylideneimine) Cobalt(II)

N,N'-4,5-dimethoxybenzenebis(3,5-di-tertiarybutylsalicylideneimine) ligand (5 mmol, 3.00 g) was added to methanol (100 mL) under an inert atmosphere, and the mixture was heated to boiling with stirring until all of the ligand was dissolved. Additional methanol was added at boiling as needed. Cobalt acetate tetrahydrate (5 mmol, 1.25 g) dissolved in methanol (40 mL) was added to the boiling solution. A dark red powder precipitates from solution. Stirring was continued as the reaction mixture was cooled to room temperature. The resulting dark red powder was collected by filtration and washed with ethanol (10 mL), and diethylether (40 mL). The product was dried under vacuum overnight to give N,N'-4,5-dimethoxybenzenebis(3,5-di-tertiarybutylsalicylideneimine)cobalt (II) in 80% yield. Analysis: Calculated for $(CoC_{38}H_{52}N_2O_4)$(MW=658): Co, 8.96; C, 69.39; H, 7.66; N, 4.26. Found: Co, 9.13; C, 66.67; H, 7.57; N, 4.23. UV-Vis.: (0.252 mM in $CH_2Cl_2$) [nm, $\epsilon \times 10^3$ $M^{-1}$ $cm^{-1}$]: 576(sh, 3.3), 531 (sh, 4.8), 467 (sh, 11.5), 407 (22.3), 390 (sh, 18.5), 363 (17.2), 314 (18.3), 303 (18.5), 250 (sh, 34.2). I.R.: [CsI, $cm^{-1}$]: 2960 (vs), 2910 (s), 2868 (m), 1612 (s), 1605 (s), 1579 (s), 1543 (s), 1521 (vs), 1505 (s), 1464 (s), 1443 (m), 1425 (m), 1409 (m), 1392 (m), 1357 (s), 1326 (w), 1282 (s), 1255 (m), 1222 (m), 1209 (m), 1191 (m), 1178 (s), 1132 (m), 1034 (w), 1013 (w), 926 (w), 915 (w), 843 (w), 821 (m), 787 (m), 537 (m), 507 (w), 491 (w). Far-I.R.: [CsI, $cm^{-1}$] 337. Magnetic moment, $\mu_{eff}^{corr}$: 300K, 3.04 B.M.; 4K, 2.97 B.M.

EXAMPLE 26

N,N'-4,5-dimethoxybenzenebis(3,5-ditertiarybutylsalicylideneimine) Manganese(III)-chloride [Mn($^t$Bu$_4$salphen)-veratrol]

N,N'-4,5-dimethoxybenzenebis(3,5-di-tertiarybutylsalicylideneimine) ligand (5 mmol, 3.00 g) was added to methanol (100 mL) under an inert atmosphere, and the mixture was heated to boiling with stirring until all of the ligand was dissolved. Additional methanol was added at boiling as needed. Manganese (II) chloride (5 mmol, 0.63 g) dissolved in methanol (40 mL) was added to the boiling solution. A dark brown powder precipitates from solution. Stirring was continued as the reaction mixture was cooled to room temperature. The resulting dark brown powder was collected by filtration and washed with ethanol (10 mL), and diethylether (40 mL). The product was dried under vacuum overnight to give N,N'-4,5-dimethoxybenzenebis(3,5-di-tertbutyl-salicylideneimine)manganese(III)-chloride in 70% yield. Analysis: Calculated for $(MnC_{38}H_{52}N_2O_4Cl)$(MW=689): Mn, 7.97; C, 66.22; H, 7.31; N, 4.06. Found: Mn, 7.18; C, 66.05; H, 7.50; N, 4.07. M.S.: ($FAB^+$ in 3-NBA) Calculated 689.215, found 688. UV-Vis.: (0.288 mM in $CH_2Cl_2$) [nm, $\epsilon \times 10^3$ $M^{-1}$ $cm^{-1}$]: 458 (br, 14.5), 378 (br, 29.5), 313(br, 24.8), 258 (41.5). I.R.: [CsI, $cm^{-1}$]: 2960 (s), 2910 (m), 2868 (m), 1606 (vs), 1563 (s), 1531 (vs), 1511 (s), 1463 (s), 1442 (m), 1425 (s), 1391 (s), 1376 (m), 1361 (s), 1310 (m), 1274 (s), 1250 (s), 1224 (s), 1211 (m), 1194 (m), 1180 (s), 1136 (s), 1110 (w), 1027 (w), 914 (w), 842 (m), 819 (w), 780 (w), 752 (w), 561 (m), 545 (m), 537 (m), 495 (w). Far-I.R.: [CsI, $cm^{-1}$] 356.6, 266.3. Magnetic moment, $\mu_{eff}^{corr}$: 300K, 5.06 B.M.; 4K, 4.88 B.M.

EXAMPLE 27

Transport studies of Crown-ether Functionalized Metal Salicylaldimine Complexes

The transport experiments consisted of two aqueous phases, a source and receiving phase, separated by a bulk liquid membrane (BLM) consisting of a chloroform solution of the carrier of interest (i.e., nickel 4,5-di(3,5-di-tertiarybutylsalicylideneimine)-benzo-18-crown-6, chloromanganese(III)-4,5-di(3,5-di-tertiarybutylsalicylideneimine)benzo-18-crown-6, etc.). The volume of the BLM was 50 mL, and the volume of each aqueous phase was 10 mL. A glass cell with an internal diameter of 53 mm was constructed with a glass wall separating the two halves (FIG. 1). A gap of 10 mm under the glass wall allows a 25 mm magnetic stir bar to rotate in the BLM phase without mixing the aqueous phases floating on the BLM. The glass wall serves to separate the phase from the source phase while maximizing the surface area between each phase and the BLM. The surface area in which each phase comes into contact is calculated to be 22 $cm^2$, and the approximate mean distance between the source and receiving phase is 3.28 cm. [The approximate mean distance between phases was calculated using 1.0 cm of depth for the chloroform on the barrier wall, and half of the 2.6 cm distance from the wall to the furthest edge of the cell. Using these two values, 1.0 and 1.3 as "a" and "b" respectively, the trigonometric expression $a^2+b^2=c^2$ was solved for c (c=1.64). Double the value of c would give the approximate mean distance between interfaces.] The aqueous phases were not continuously stirred except by the disturbing motions of the BLM phase underneath. It has been observed that when stirring of the aqueous phase occurs due to a vortex forming in the chloroform phase, either enhanced transport or mechanical transport occurs. Efforts to eliminate vortexes were made to ensure the comparability of al cells sampled.

The cell was loaded by addition of the BLM without stirring. The receiving phase was then carefully floated in its chamber atop the BLM. Timing was initiated when the first drop of source phase touched the BLM. The whole 10 mL of source phase was added quickly but carefully over about 40 seconds. After addition of the source phase, the cell was stirred, and capped with a petri dish to minimize volume loss in the aqueous phases due to evaporation.

Time zero was marked upon the addition of stock tryptophan solution (50 mM) to the first cell. The transport studies were carried out at ambient temperature in systems where a compartment containing aqueous 50 mM tryptophan solution (10 mL) is separated from a compartment containing pure water (10 mL) by a layer of 7.2 mM $CHCl_3$ solution (50 mL) containing the carriers (i.e., crown-ether functionalized salicylaldimine complexes). All cells were sampled sequentially in the same order they were loaded. Time was kept using a digital stopwatch obtained from Fisher Scientific (Fisher Catalog #14-649-11), with a resolution of 0.01 second for the first 30 minutes, and 1.00 second for 24 hours. All times are recorded within experimental error of ±2 minutes. The starting pH of all tryptophan solutions was approximately 6.0. All experiments were conducted at room temperature; however thermal warming from the stirring plates tended to warm the solutions. Temperature of the chloroform layer were typically 28.0° C. (±0.2° C.) as determined experimentally.

The concentration of the transported tryptophan was monitored by electronic spectroscopy except when a mixture of 5 amino acids was used (i.e., the initial concentration of each amino acid was 10 mM), in which case the quantity transported was established by $^1$H-NMR spectroscopy. Samples for measurement on the Cary 1E UV-Vis Spectrophotometer were extracted by glass pipette after gentle stirring of the aqueous receiving phase. Stirring was required to ensure homogeneity of the solution as well as consistency of the sample extracted. Samples were taken from the cells in the same order the cells were loaded each time to minimize time discrepancies. The sample was scanned, and the peak of interest marked precisely using the scrolling cursor. All samples were background corrected for a blank sample of deionized water. Calibration of the UV-Vis absorption measurements was accomplished using serial dilutions to generate a Beer's Law plot which gave the extinction coefficient for tryptophan at 278 nm as 5000 M-1 cm-2 which is consistent with the known literature value (Bailey, J. L., *Techniques in Protein Chemistry* 2nd Ed.). The extinction coefficient was then used to calculate the measured experimental concentrations from the observed absorbances in the receiving phase.

We claim:

1. A compound, comprising first and second chelating groups linked via a linker group, said first chelating group comprising a crown ether, said second chelating group comprising a salicylaldimine ligand modified with a hydrophobic group, wherein said compound is capable of transporting one or more amino acids or amino acid derivatives at a flux greater than $5\times10^{-3}$ mol/m$^2$-sec·mol$_{carrier}$.

2. The compound of claim 1, wherein said linker comprises a phenyl bridge.

3. The compound of claim 1, further comprising a counterion.

4. The compound of claim 1, wherein said counterion is a halide selected from the group consisting of chloride, bromide and iodide ions.

5. The compound of claim 1, wherein said hydrophobic group comprises tertiary butyl groups.

6. The compound of claim 1, wherein said salicylaldimine is 4,5-di(3,5-ditertiarybutylsalicylideneimine).

7. The compound of claim 1, wherein said crown ether is 18-benzo-crown-6.

8. The compound of claim 1, wherein said salicylaldimine is complexed to a metal ion.

9. The compound of claim 8, wherein said metal ion is selected from the group consisting of manganese(III), nickel (II), cobalt(II), copper(II) and iron(III).

10. The compound of claim 1, wherein said crown ether is complexed with alkali cations.

11. The compound of claim 10, wherein said alkali cations is selected from the group consisting of potassium and cesium.

12. The compound of claim 1, wherein said compound is capable of transporting dopamine at a flux greater than $5\times10^{-2}$ mol/m$^2$-sec·mol$_{carrier}$.

13. A transport system, comprising a compound contained within a liposome, said compound comprising first and second chelating groups linked via a linker group, said first chelating group comprising a crown ether, said second chelating group comprising a salicylaldimine ligand modified with a hydrophobic group, wherein said compound is capable of transporting one or more amino acids or amino acid derivatives at a flux greater than $5\times10^{-3}$ mol/m$^2$-sec·mol$_{carrier}$.

14. The transport system of claim 13, wherein said linker comprises a phenyl bridge.

15. The transport system of claim 13, wherein said hydrophobic group comprise tertiary butyl groups.

16. The compound of claim 13, wherein said salicylaldimine is 4,5-di(3,5-ditertiarybutylsalicylideneimine).

17. The transport system of claim 13, wherein said crown ether is 18-benzo-crown-6.

18. The compound of claim 13, wherein said salicylaldimine is complexed to a metal ion.

19. The transport system of claim 18, wherein said metal ion is selected from the group consisting of manganese(III), nickel(II), cobalt(II), copper(II) and iron(III).

20. The transport system of claim 13, wherein said crown ether is complexed with alkali cations.

21. The transport system of claim 20, wherein said alkali cations is selected from the group consisting of potassium and cesium.

22. The transport system of claim 13, wherein said compound is capable of transporting dopamine at a flux greater than $5\times10^{-2}$ mol/m$^2$-sec·mol$_{carrier}$.

* * * * *